United States Patent [19]

Müller et al.

[11] Patent Number: 4,551,464
[45] Date of Patent: Nov. 5, 1985

[54] ANTITHROMBOTIC SULFOXIMINO CARBOSTYRILS

[75] Inventors: Erich Müller; Josef Nickl; Berthold Narr; Josef Roch; Walter Haarmann; Johannes M. Weisenberger, all of Biberach, Fed. Rep. of Germany

[73] Assignee: Dr. Karl Thomae Gesellschaft mit beschränkter Haftung, Biberach an der Riss, Fed. Rep. of Germany

[21] Appl. No.: 573,964

[22] Filed: Jan. 26, 1984

Related U.S. Application Data

[63] Continuation of Ser. No. 395,631, Jul. 6, 1982, Pat. No. 4,442,111.

[30] Foreign Application Priority Data

Jul. 25, 1981 [DE] Fed. Rep. of Germany ....... 3129444
Oct. 29, 1981 [DE] Fed. Rep. of Germany ....... 3142904

[51] Int. Cl.$^4$ ..................... A61K 31/47; C07D 215/22
[52] U.S. Cl. .................................. 514/312; 546/157; 546/158
[58] Field of Search ................. 546/157, 158; 424/258

[56] References Cited

U.S. PATENT DOCUMENTS 4,442,111  4/1984  Müller ................................ 424/263

OTHER PUBLICATIONS

Burger "Medicinal Chemistry" 2nd Edition p. 42.

Primary Examiner—Robert Gerstl
Assistant Examiner—Robert Benson
Attorney, Agent, or Firm—Hammond & Littell, Weissenberger & Dippert

[57] ABSTRACT

Compounds of the formula

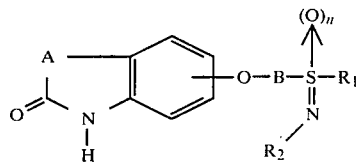

wherein
n is 0 or 1;
A is methylene, vinylene or ethylene optionally substituted by lower alkyl;
B is alkylene;
$R_1$ is an optionally substituted alkyl, phenyl or naphthyl group, or a cycloalkyl or pyridyl group; and
$R_2$ is hydrogen or acyl;

and non-toxic, pharmacologically acceptable acid addition salts thereof. The compounds as well as their salts are useful as antithrombotics.

7 Claims, No Drawings

ANTITHROMBOTIC SULFOXIMINO CARBOSTYRILS

This is a continuation of copending application Ser. No. 395,631, filed July 6, 1982, now U.S. Pat. No. 4,442,111.

This invention relates to novel sulfimines and salts thereof, to methods of preparing these compounds, to pharmaceutical compositions containing them as active ingredients, and to methods of using them as antithrombotics.

More particularly, the present invention relates to a novel class of compounds represented by the formula

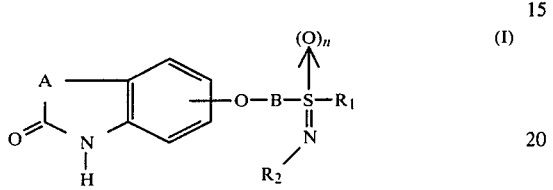

wherein
n is 0 or 1;
A is methylene, vinylene or ethylene, each optionally mono- or di-substituted with alkyl groups of 1 to 3 carbon atoms each;
B is straight or branched alkylene of 2 to 6 carbon atoms;
$R_1$ is alkyl of 1 to 3 carbon atoms; (unsubstituted or monosubstituted phenyl)-(alkyl of 1 to 3 carbon atoms) or unsubstituted or monosubstituted phenyl where the substituent on the phenyl ring is alkyl of 1 to 4 carbon atoms, halogen, alkoxy of 1 to 3 carbon atoms, cyclohexyl, phenyl, halophenyl, alkyl of 4 to 7 carbon atoms, cycloalkyl of 3 to 7 carbon atoms, di- or tri-(alkyl of 1 to 4 carbon atoms)-phenyl, di- or tri-(alkoxy of 1 to 3 carbon atoms)-phenyl, hydroxyl or amino-(disubstituted phenyl) where the substituents are each alkyl of 1 to 4 carbon atoms, alkoxy of 1 to 3 carbon atoms or halogen; naphthyl; (alkoxy of 1 to 3 carbon atoms)-naphthyl; or pyridyl; and
$R_2$ is hydrogen or an acyl group of an organic carboxylic acid, an organic or inorganic sulfonic acid or a carbonic acid derivative;
and non-toxic, pharmacologically acceptable acid addition salts thereof.

The term "an acyl group" used in the definition of substituent $R_2$ refers, more particularly, to the acyl group of an aliphatic saturated or unsaturated alkanoic acid, which may optionally be substituted, an optionally substituted aromatic carboxylic acid in which a —CH═CH— group or 1 or 2 —CH— groups may each be replaced by an oxygen, sulfur or nitrogen atom, or it is the acyl group of a carbonic acid ester, or of an optionally substituted carbamic acid, or an aliphatic or aromatic sulfonic acid or the hydroxysulfonyl group.

The term "halogen" used in the definition of substituent $R_1$ refers, in particular, to fluorine, chlorine or bromine.

Specific examples of variables A, B, $R_1$ and $R_2$ in formula I are the following:
A: Methylene, methylmethylene, dimethylmethylene, diethylmethylene, dipropylmethylene, vinylene, methylvinylene or ethylene;
B: Ethylene, n-propylene, n-butylene, n-pentylene, n-hexylene, 1-methyl-ethylene, 2-methyl-ethylene, 1-methyl-n-propylene, 2-methyl-n-propylene, 3-methyl-n-propylene, 1-methyl-n-butylene, 2-methyl-n-butylene, 3-methyl-n-butylene, 4-methyl-n-butylene, 1-methyl-n-pentylene, 2-methyl-n-pentylene, 3-methyl-n-pentylene, 4-methyl-n-pentylene, 5-methyl-n-pentylene, 1,1-dimethyl-ethylene, 1,2-dimethyl-ethylene, 2,2-dimethylethylene, 1,1-dimethyl-n-propylene, 2,2-dimethyl-n-propylene, 3,3-dimethyl-n-propylene, 1,2-dimethyl-n-propylene, 1,3-dimethyl-n-propylene, 1,1-dimethyl-n-butylene, 2,2-dimethyl-n-butylene, 3,3-dimethyl-n-butylene, 4,4-dimethyl-n-butylene, 1,2-dimethyl-n-butylene, 1,3-dimethyl-n-butylene, 1,4-dimethyl-n-butylene, 2,3-dimethyl-n-butylene, 1-ethyl-ethylene, 2-ethyl-ethylene, 1-ethyl-n-propylene, 2-ethyl-n-propylene, 3-ethyl-n-propylene, 1-ethyl-n-butylene, 2-ethyl-n-butylene, 3-ethyl-n-butylene, 4-ethyl-n-butylene, 1-methyl-2-ethyl-ethylene, 1-methyl-2-ethyl-n-propylene, 1-methyl-3-ethyl-n-propylene, 1-methyl-2-propyl-ethylene, 1-propyl-ethylene, 1-butyl-ethylene or 1-propyl-n-propylene;
$R_1$: Methyl, ethyl, propyl, isopropyl, butyl, isobutyl, tert. butyl, pentyl, neopentyl, tert. pentyl, hexyl, heptyl, benzyl, 1-phenylethyl, 2-phenylethyl, 1-phenylpropyl, 3-phenylpropyl, fluorobenzyl, chlorobenzyl, bromobenzyl, methylbenzyl, isopropylbenzyl, methoxybenzyl, ethoxybenzyl, cyclopropyl, cyclobutyl, cyclopentyl, cyclohexyl, cycloheptyl, phenyl, fluorophenyl, chlorophenyl, bromophenyl, methylphenyl, dimethylphenyl, isopropylphenyl, tert. butylphenyl, methoxyphenyl, ethoxyphenyl, propoxyphenyl, cyclohexylphenyl, diphenylyl, fluorophenyl-phenyl, chlorophenyl-phenyl, difluorophenyl, dichlorophenyl, dibromophenyl, dimethoxyphenyl, methoxychlorophenyl, methoxy-bromophenyl, methyl-tert.butyl-phenyl, methyl-chlorophenyl, methylbromophenyl, tert.-butyl-bromophenyl, dichloroaminophenyl, dibromo-aminophenyl, dimethyl-aminophenyl, dichloro-hydroxyphenyl, dibromo-hydroxyphenyl, dimethyl-hydroxyphenyl, di-tert.butyl-hydroxyphenyl, trimethoxy-phenyl, naphthyl, methoxynaphthyl or pyridyl; and
$R_2$: hydrogen, formyl, acetyl, propionyl, pivaloyl, pentanoyl, hexanoyl, heptanoyl, octanoyl, nonanoyl, methoxyacetyl, methoxypropionyl, pinanoyl, benzoyl, fluorobenzoyl, chlorobenzoyl, bromobenzoyl, cyanobenzoyl, methylbenzoyl, ethylbenzoyl, isopropylbenzoyl, tert. butylbenzoyl, difluorobenzoyl, dichlorobenzoyl, dimethylbenzoyl, trimethylbenzoyl, naphthoyl, pyridinoyl, thenoyl, acetoxy-benzoyl, hydroxysulfonyl, methylsulfonyl, ethylsulfonyl, camphorsulfonyl, phenylsulfonyl, methylphenylsulfonyl, fluorophenylsulfonyl, chlorophenylsulfonyl, bromophenylsulfonyl, pentamethylphenylsulfonyl, naphthylsulfonyl, methoxycarbonyl, ethoxycarbonyl, propoxycarbonyl, isopropoxycarbonyl, benzyloxycarbonyl, aminocarbonyl, methylaminocarbonyl, dimethylaminocarbonyl, phenylaminocarbonyl or chlorophenylaminocarbonyl.

Preferred compounds of the formula I above are those wherein
n is 0 or 1;
A is dimethylmethylene, vinylene or ethylene;
B is straight alkylene of 3 to 5 carbon atoms;

$R_1$ is alkyl of 1 to 6 carbon atoms, benzyl, phenylethyl, cyclohexyl, naphthyl, methoxy-naphthyl, pyridyl, phenyl optionally substituted by alkyl of 1 to 4 carbon atoms or by methoxy, cyclohexyl, phenyl, fluorophenyl, fluorine, chlorine or bromine, phenyl disubstituted by alkyls of 1 to 4 carbon atoms, methoxy, chlorine and/or bromine atoms, where the substituents of the phenyl nucleus may be the same or different, or an aminophenyl, hydroxyphenyl or methoxyphenyl group substituted by two chlorine or bromine atoms, two methoxy groups or two alkyl groups each of 1 to 4 carbon atoms; and $R_2$ is hydrogen, alkanoyl of 1 to 8 carbon atoms optionally substituted by a methoxy group, a benzoyl or phenylsulfonyl group optionally substituted by a halogen atom or by a cyano group or by an alkyl group of 1 to 4 carbon atoms, an alkoxycarbonyl group with a total of 2 to 4 carbon atoms, an aminocarbonyl group substituted by a chlorophenyl group or by 1 or 2 methyl groups, or a naphthoyl, pinanoyl, camphorsulfonyl, pentamethylphenylsulfonyl, pyridinoyl group or thenoyl group;

and non-toxic, pharmacologically acceptable addition salts thereof formed with strong acids.

Particularly preferred compounds of the formula I above are those wherein n is 1;

A is dimethylmethylene, vinylene or ethylene;

B is n-butylene;

$R_1$ is methyl, methoxynaphthyl, a phenyl group optionally substituted by a methoxy group or a fluorine or chlorine atom, a phenyl group substituted by 2 chlorine or bromine atoms, methylbromophenyl, 4-amino-3,5-dibromophenyl or di-tert. butylhydroxyphenyl; and $R_2$ is hydrogen, an alkanoyl group of 1 to 3 carbon atoms or a benzoyl or phenylsulfonyl group optionally substituted by an alkyl group of 1 to 4 carbon atoms;

and non-toxic, pharmacologically acceptable addition salts thereof formed with strong acids.

The novel compounds may be prepared by the following methods:

METHOD A

For the preparation of a compound of the formula I wherein n is 1 and $R_2$ is hydrogen, by reacting a sulfoxide of the formula

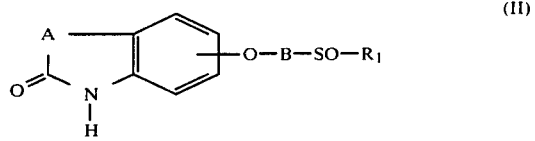

(II)

wherein A, B and $R_1$ have the meanings previously defined, with hydrazoic acid optionally formed in the reaction mixture.

The reaction is advantageously carried out in a solvent or mixture of solvents such as methylene chloride, dimethylformamide or tetrahydrofuran, and at temperatures between 0° and 40° C., preferably between 10° and 35° C. It is particularly advantageous to carry out the reaction with an alkali metal azide, such as sodium azide, and polyphosphoric acid as the solvent.

METHOD B

For the preparation of a compound of the formula I wherein $R_2$ is hydrogen, by reacting a compound of the formula

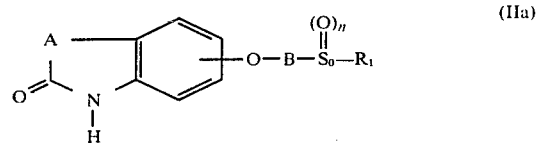

(IIa)

wherein A, B, n and $R_1$ have the meanings previously defined, with a compound of the formula

$$H_2N-O-X-R_3 \quad (III)$$

wherein

X is carbonyl or sulfonyl, and $R_3$ is an aryl group disubstituted in the o-position, such as a 2,4,6-trimethylphenyl or 2,4,6-triisopropylphenyl group, or also hydroxyl when X is sulfonyl.

The reaction is advantageously carried out in a solvent or a mixture of solvents such as methylene chloride, chloroform, dimethylformamide, tetrahydrofuran or dioxane at temperatures between 0° and 50° C., preferably between 5° and 40° C. However, in a particularly advantageous embodiment of the reaction, the compound of the formula III is used without being isolated beforehand or is prepared in the reaction mixture.

METHOD C

For the preparation of a compound of the formula I wherein n is 1, by oxidizing a mercapto compound of the formula

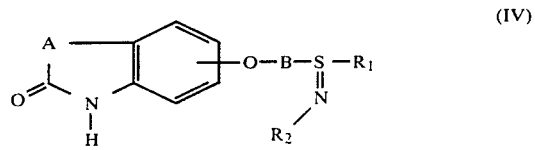

(IV)

wherein A, B, $R_1$ and $R_2$ have the meanings previously defined.

The oxidation is preferably carried out in a solvent or mixture of solvents, for instance in water, water/pyridine, methanol, ethanol, acetone, formic acid, glacial acetic acid, trifluoroacetic acid or dilute sulfuric acid, at temperatures between −80° and 100° C., depending on the particular oxidizing agent which is used. It is particularly advantageous to carry out the reaction with one equivalent of the oxidizing agent, for example with hydrogen peroxide in glacial acetic acid or formic acid at 0° to 20° C. or in acetone at 0° to 60° C., with a peracid such as performic acid in glacial acetic acid or trifluoroacetic acid at 0° to 50° C., or with sodium metaperiodate in aqueous methanol or ethanol at 15° to 25° C.

METHOD D

For the preparation of a compound of the formula I wherein $R_2$ is other than hydrogen:

By acylating a compound of the formula

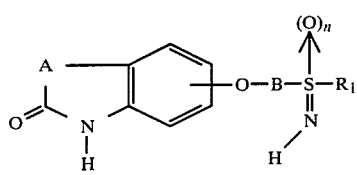 (V)

wherein n, A, B and $R_1$ have the meanings previously defined.

The reaction is advantageously carried out in a solvent or mixture of solvents, such as water, methylene chloride, chloroform, ether, tetrahydrofuran, dioxane or dimethylformamide, with a corresponding acylating agent, for instance with an acid in the presence of an acid-activating or dehydrating agent such as thionyl chloride, with an anhydride thereof such as acetic acid anhydride, with an ester thereof such as ethyl p-toluenesulfonate or diethyl carbonate, with a halide thereof such as acetyl chloride, ethyl chloroformate or p-toluenesulfonic acid chloride, or with a corresponding isocyanate, where these may optionally also be used as solvents, optionally in the presence of an inorganic or tertiary organic base, such as sodium hydroxide, potassium carbonate, triethylamine or pyridine, where the latter may simultaneously also serve as solvents, at temperatures between $-25°$ and $100°$ C., preferably between $-10°$ and $18°$ C.

METHOD E

By reacting a compound of the formula

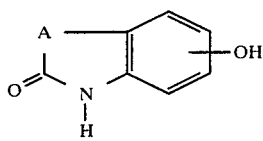 (VI)

wherein A has the meanings previously defined, or a salt thereof formed with an inorganic or tertiary organic base, with a compound of the formula

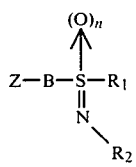 (VII)

wherein n, $R_1$, $R_2$ and B have the meanings previously defined, and

Z is a nucleophilically exchangeable group, such as a halogen atom or a sulfonic acid ester group, for instance a chlorine, bromine or iodine atom or a p-toluenesulfonyloxy or methanesulfonyloxy group.

The reaction is advantageously carried out in a suitable solvent or mixture of solvents such as dioxane, tetrahydrofuran, chloroform or toluene, but preferably in an anhydrous aprotic solvent such as acetone, dimethylformamide or dimethylsulfoxide, optionally in the presence of an alkali metal base such as sodium carbonate, potassium carbonate or sodium hydroxide, at temperatures between 0° C. and the boiling point of the solvent which is used, for instance at temperatures between 0° and 100° C., preferably between 10° and 50° C. The reaction may, however, also be carried out without a solvent.

METHOD F

For the preparation of a compound of the formula I wherein n is O.

By reacting a thioether of the formula

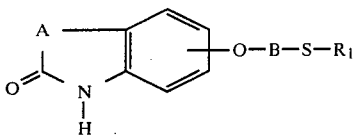 (VIII)

wherein A, B and $R_1$ have the meanings previously defined, with an amide of the formula

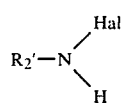 (IX)

wherein

Hal is chlorine or bromine, and $R_2'$ has the meanings previously defined for $R_2$, except hydrogen, or with an alkali metal salt thereof, optionally followed by hydrolysis.

The reaction is preferably carried out with an alkali metal salt of a compound of the formula IX, such as the sodium salt, optionally in the presence of an inorganic base such as an alkali metal base, in a solvent or mixture of solvents, such as methanol, methanol/water or ethanol, advantageously at temperatures between 0° and 80° C., preferably between 5° and 50° C.

The optional subsequent hydrolysis is carried out in the presence of an acid or base, preferably in the presence of a base such as sodium hydroxide, in a solvent or mixture of solvents such as water, methanol, water/methanol or tetrahydrofuran/water, and at temperatures up to the boiling point of the solvent which is used.

The compounds of the formula I are basic and therefore form addition salts with strong acids. Examples of non-toxic, pharmacologically acceptable acid addition salts are those formed with hydrochloric acid, sulfuric acid, mesitylene-sulfonic acid or the like.

The starting compounds of the formulas II to IX are either disclosed in the literature or may be prepared by methods described in the literature.

Thus, for example, the starting compounds of the formulas II and IIa are disclosed in published European application No. 3,771 and German Offenlegungsschrift No. 3,042,632 or may be prepared by the process described in European application No. 3,771.

The starting compounds of the formula III are preferably prepared by reacting a corresponding O-carbonyl- or O-sulfonyl-acethydroxamic acid ester with sulfuric acid and subsequent extraction, after the addition of a base.

The mercapto starting compounds of the formula IV are obtained, for example, by reacting a corresponding thioether with a chloroamine or with O-mesitylenesulfonyl-hydroxylamine.

A starting compound of the formula V may be obtained, for example, by oxidation of a corresponding mercapto compound which is prepared by reacting a corresponding thioether with a chloroamine and subsequent hydrolysis, or by reacting a corresponding mercapto or sulfinyl compound with O-mesitylenesulfonyl-hydroxylamine.

A starting compound of the formula VII may be obtained, for example, by reacting a corresponding sulfinyl compound (obtained by oxidation of a corresponding thioether) with a corresponding O-mesitylenesulfonyl-hydroxylamine and optional subsequent acylation.

A starting compound of the formula VIII may be obtained, for example, by reacting a corresponding hydroxy or mercapto compound with a corresponding halide in the presence of a base.

A starting compound of the formula IX may be obtained, for example, by reacting a corresponding amide with a hypohalite.

The following examples illustrate the present invention and will enable others skilled in the art to understand it more completely. It should be understood, however, that the invention is not limited solely to the particular examples given below.

EXAMPLE 1

6-(4-Phenylsulfoximino-butoxy)-3,4-dihydrocarbostyril

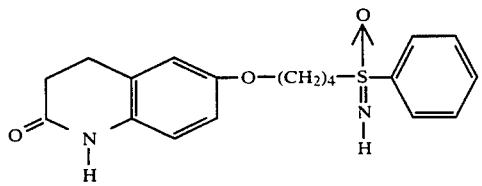

3.4 gm (0.01 mol) of 6-(4-phenylsulfinyl-butoxy)-b 3,4-dihydrocarbostyril were stirred into 50 ml of polyphosphoric acid at 45° C. After virtually all of it had dissolved, 0.98 gm (0.015 mol) of sodium azide was added in small batches over a period of 30 minutes. A slight evolution of nitrogen gas was observed. The beige-colored, creamy-foamy mass was stirred for 3 hours at 45°–50° C. and then 150 gm of ice were added. The cloudy solution formed thereby was adjusted to pH 8 with concentrated ammonia, and the precipitated resinous product was extracted with chloroform. The oily evaporation residue was recrystallized from ethyl acetate. White crystals were obtained.

Melting point: 127°–129° C.

Yield: 1.6 gm (44.6% of theory).

EXAMPLE 2

6-[4-(3,4-dichlorophenyl-sulfoximino)-butoxy]-3,4-dihydrocarbostyril 24.0 gm (0.84 mol) of ethyl o-mesitylenesulfonyl-acethydroxamate were dissolved in 35 ml of dioxane and 17 ml of 90% sulfuric acid were added dropwise, while stirring, at 20°–23° C. over a period of 20 minutes. The mixture was stirred for 10 minutes more at the same temperature, then poured into 300 ml of ice-cold water, and the O-mesitylenesulfonyl-hydroxylamine formed thereby was extracted with 100 ml of methylenechloride, washed twice more with ice-cold water and dried over magnesium sulfate. 12.4 gm (0.03 mol) of 6-[4-(3,4-dichlorophenyl-sulfinyl)-butoxy]-3,4-dihydrocarbostyril were added to the extract solution thus obtained, and the mixture was stirred for 18 hours at room temperature. The resulting crystal slurry, which is just barely stirrable, was diluted with 120 ml of ethylacetate, and then the crystalline 6-[4-(3,4-dichlorophenyl-ulfoximino]-3,4-dihydrocarbostyril mesitylene-sulfonate was suction-filtered off. To obtain the free base, this salt was suspended in 60 ml of methanol and stirred with 17 ml of 2N sodium hydroxide, whereupon everything went into solution. After a short time, a white precipitate was obtained, which consisted of 6-[4-(3,4-dichlorophenyl-sulfoximino)-butoxy]-3,4-dihydrocarbostyril.

Melting point: 160°–161° C.

Yield: 10.4 gm (81.1% of theory).

EXAMPLE 3

6-[4-(4-tert.butylphenyl-sulfoximino)-butoxy]-3,4-dihydrocarbostyril

This compound was prepared analogous to Example 2 from 6-[4-(4-tert. butylphenyl-sulfinyl)-butoxy]-3,4-dihydrocarbostyril and O-mesitylenesulfonyl-hydroxylamine.

Melting point: 201°–203° C.

Yeild: 44% of theory.

EXAMPLE 4

6-[4-(3,5-Di-tert.butyl-4-hydroxy-phenyl-sulfoximino)-utoxy]-3,4-dihydrocarbostyril This compound was prepared analogous to Example 2 from 6-[4-(3,5-di-tert.butyl-4-hydroxyphenyl-sulfinyl)-butoxy]-3,4-dihydrocarbostyril and O-mesitylenesulfonyl-hydroxylamine.

Melting point: 110°–112° C.

Yield: 52% of theory.

EXAMPLE 5

6-[4-(4-Cyclohexylphenyl-sulfoximino)-butoxy]-3,4-dihydrocarbostyril

This compound was prepared analogous to Example 2 from 6-[4-(4-cyclohexylphenyl-sulfinyl)-butoxy]-3,4-dihydrocarbostyril and O-mesitylenesulfonyl-hydroxylamine.

Melting point: 174°–176° C.

Yield: 65% of theory.

EXAMPLE 6

6-[4-(4-Biphenylyl-sulfoximino)-butoxy]-3,4-dihydrocarbostyril

This compound was prepared analogous to Example 2 from 6[4-(4-biphenylyl-sulfinyl)-butoxy]-3,4-dihydrocarbostyril and O-mesitylenesulfonyl-hydroxylamine.

Melting point: 184°–186° C.

Yield: 64% of theory.

EXAMPLE 7

6-[4-(Naphthyl-(2)-sulfoximino)-butoxy]-3,4-dihydrocarbostyril

This compound was prepared analogous to Example 2 from 6-[4-(naphthyl-2-sulfinyl)-butoxy]-3,4-dihydrocarbostyril and O-mesitylenesulfonyl-hydroxylamine.

Melting point: 151°–152° C.

Yield: 71% of theory.

EXAMPLE 8

6-[4-(4-fluorophenyl-sulfoximino)-butoxy]-3,4-dihydrocarbostyril

This compound was prepared analogous to Example 1 from 6-[4-(4-fluorophenyl sulfinyl)-butoxy]-3,4-dihydrocarbostyril and sodium azide in polyphosphoric acid.

Melting point: 170°–173° C.
Yield: 78% of theory.

EXAMPLE 9

6-[4-(4-chlorophenyl-sulfoximino)-butoxy]-3,4-dihydrocarbostyril

This compound was prepared analogous to Example 2 from 6-]4-(4-chlorophenyl-sulfinyl)-butoxy]3,4-dihydrocarbostyril and O-mesitylenesulfonyl-hydroxylamine.

Melting point: 150°–151° C.
Yield: 60% of theory.

EXAMPLE 10

6-[4-(3-methyl-4-bromophenyl-sulfoximino)-butoxy]-3,4- dihydrocarbostyril

This compound was prepared analogous to Example 2 from 6-[4-(3-methyl-4-bromophenyl-sulfinyl)-butoxy]-b 3,4-dihydrocarbostyril and O-mesitylenesulfonyl-hydroxylamine.

Melting point: 150°–152° C.
Yield: 60% of theory.

EXAMPLE 11

6-[4-(3,5-dibromo-4-aminophenyl-sulfoximino)-butoxy]-3,4-dihydrocarbostyril

This compound was prepared analogous to Example 2 from 6-[4-(3,4-dibromo-4-aminophenyl-sulfinyl)-butoxy]-3,4 -dihydrocarbostyril and O-mesitylenesulfonyl-hydroxylamine.

Melting point: 110°–113° C.
Yield: 55% of theory.

EXAMPLE 12

6-(4-phenylsulfoximino-butoxy)-carbostyril

This compound was prepared analogous to Example 2 from 6-(4-phenylsulfinyl-butoxy)-carbostyril and O-mesitylenesulfonyl hydroxylamine.

Melting point: 161°–162° C.
Yield: 60% of theory.

EXAMPLE 13

6-[4-(4-tert.butylphenyl-sulfoximino)-butoxy]-carbostyril

This compound was prepared analogous to Example 1 from 6-[4-(4-tert. butylphenyl-sulfinyl)-butoxy]-carbostyril and sodium azide in polyphosphoric acid.

Melting point: 208°–210° C.
Yield: 45% of theory.

EXAMPLE 14

6-[4-(3,5-Di-tert. butyl-4-hydroxyphenyl-sulfoximino)-butoxy]-carbostyril

This compound was prepared analogous to Example 2 from 6-[4-(3,4-di-tert.butyl-4-hydroxyphenyl-sulfinyl)-butoxy]-carbostyril and O-mesitylenesulfonyl-hydroxylamine.

Melting point: 205°–207° C.
Yield: 59% of theory.

EXAMPLE 15

6-[4-Cyclohexylphenyl-sulfoximino)-butoxy]-carbostyril

This compound was prepared analogous to Example 1 from 6-[4-(4-cyclohexylphenyl-sulfinyl)-butoxy]-carbostyril and sodium azide in polyphosphoric acid.

Melting point: 195°–197° C.
Yield: 52% of theory.

EXAMPLE 16

6-[4-(4-Biphenylyl-sulfoximino)-butoxy]-carbostyril

This compound was prepared analogous to Example 2 from 6-[4-(4-biphenylyl-sulfinyl)-butoxy]-carbostyril and O-mesitylenesulfonyl-hydroxylamine.

Melting point: 236°–238° C.
Yield: 76% of theory.

EXAMPLE 17

6-(4-Cyclohexylsulfoximino-butoxy)-carbostyril

This compound was prepared analogous to Example 1 from 6-(4-cyclohexylsulfinyl-butoxy)-carbostyril and sodium azide in polyphosphoric acid.

Melting point: 145°–147° C.
Yield: 47% of theory.

EXAMPLE 18

6-[4-(4-Fluorophenyl-sulfoximino)-butoxy]-carbostyril

This compound was prepared analogous to Example 2 from 6-[4-(4-fluorophenyl-sulfinyl)-butoxy]- carbostyril and O-mesitylenesulfonyl-hydroxylamine.

Melting point: 177°–179° C.
Yield: 70% of theory.

EXAMPLE 19

6-[4-(4-chlorophenyl-sulfoximino)-butoxy]-carbostyril

This compound was prepared analogous to Example 2 from 6-[4-(4-chlorophenyl-sulfinyl)-butoxy]-carbostyril and O-mesitylenesulfonyl-hydroxylamine.

Melting point: 201°–203° C.
Yield: 79% of theory.

EXAMPLE 20

6-[4-(4-Bromophenyl-sulfoximino)-butoxy]-carbostyril

This compound was prepared analogous to Example 2 from 6-[4-(4-bromophenyl-sulfinyl)-butoxy]-carbostyril and O-mesitylenesulfonyl-hydroxylamine.

Melting point: 211°–213° C.
Yield: 63% of theory.

EXAMPLE 21

6-[4-(3,4-Dichlorophenyl-sulfoximino)-butoxy]-carbostyril

This compound was prepared analogous to Example 2 and 6-[4-(3,4-dichlorophenyl-sulfinyl)-butoxy]-carbostyril and O-mesitylenesulfonyl-hydroxylamine.

Melting point: 214°–216° C.
Yield: 73% of theory.

EXAMPLE 22

6-4-(3-Methyl-4-bromophenyl-sulfoximino)-butoxy]-carbostyril

This compound was prepared analogous to Example 1 from 6-[4-(3-methyl-4-bromophenyl-sulfinyl)-butoxy]-carbostyril and sodium azide in polyphosphoric acid.

Melting point: 193°–194° C.
Yield: 54% of theory.

EXAMPLE 23

6-[4-(2'-Fluoro-4-biphenylyl-sulfoximino)-butoxy]-carbostyril

This compound was prepared analogous to Example 2 from 6-[4-(2'-fluoro-4-biphenylyl-sulfinyl)-butoxy]-carbostyril and O-mesitylenesulfonyl-hydroxylamine.

Melting point: 191°–193° C.
Yield: 74% of theory.

EXAMPLE 24

6-[4-(3,5-Dibromo-4-aminophenyl-sulfoximino)-butoxy]-carbostyril

This compound was prepared analogous to Example 2 from 6-[4-(3,5-dibromo-4-aminophenyl-sulfinyl)-butoxy]-carbostyril and O-mesitylenesulfonyl-hydroxylamine.

Melting point: 130°–135° C.
Yield: 51% of theory.

EXAMPLE 25

3,3-Dimethyl-5-[4-(4-methylphenyl-sulfoximino)-butoxy]-indolinone-2

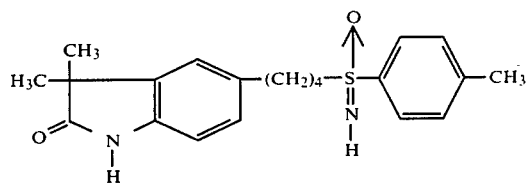

This compound was prepared analogous to Example 2 from 3,3-dimethyl-5-[4-(4-methylphenylsulfinyl)-butoxy]-indolinone-2 and O-mesitylenesulfonyl-hydroxylamine.

Melting point: 146°–147° C.
Yield: 84% of theory.

EXAMPLE 26

3,3-Dimethyl-5-[4-(4-tert.butylphenyl-sulfoximino)-butoxy]-indolinone-2

This compound was prepared analogous to Example 2 from 3,3-dimethyl-5-[4-(4-tert.butylphenyl-sulfinyl)-butoxy]-indolinone-2 and O-mesitylenesulfonyl-hydroxylamine.

Melting point: 195°–197° C.
Yield: 85% of theory.

EXAMPLE 27

3,3-Dimethyl-5-[4-(2-methyl-4-tert.butylphenyl-sulfoximino)-butoxy]-indolinone-2

This compound was prepared analogous to Example 2 from 3,3-dimethyl-5-[4-(2-methyl-4-tert.butylphenyl-sulfinyl)-butoxy]-indolinone-2 and O-mesitylenesulfonyl-hydroxylamine.

Melting point: 149°–150° C.
Yield: 26% of theory.

EXAMPLE 28

3,3-Dimethyl-5-[4-(3,5-di-tert.butyl-4-hydroxyphenyl-sulfoximino)-butoxy]-indolinone-2

This compound was prepared analogous to Example 2 from 3,3-dimethyl-5-[4-(3,5-di-tert.butyl-4-hydroxyphenyl-sulfoximino)-butoxy]-indolinone-2 and O-mesitylenesulfonylhydroxylamine.

Glassy substance.
$R_f$ value: 0.25 (silicagel plate; Eluant: ethyl acetate/methylene chloride 1:1).
Yield: 42% of theory.

EXAMPLE 29

[3,3-Dimethyl-5-[4-(cyclohexylphenyl-sulfoximino)-butoxy]-indolinone-2

This compound was prepared analogous to Example 1 from 3,3-dimethyl-5-[4-(cyclohexylphenyl-sulfinyl)-butoxy]-indolinone-2 and sodium azide in polyphosphoric acid.

Melting point: 162°–163° C.
Yield: 39% of theory.

EXAMPLE 30

3,3-Dimethyl-5-[4-(2-naphthyl-sulfoximino)-butoxy]-indolinone-2

This compound was prepared analogous to Example 2 from 3,3-dimethyl-5-[4-(2-naphthyl-sulfinyl)-butoxy]-indolinone-2 and O-mesitylenesulfonyl-hydroxylamine.

Melting point: 120°–121° C.
Yield: 64% of theory.

EXAMPLE 31

3,3-dimethyl-5-[4-(cyclohexyl-sulfoximino)-butoxy]-indolinone-2

This compound was prepared analogous to Example 2 from 3,3-dimethyl-5-[4-(cyclohexyl-sulfinyl)-butoxy]-indolinone-2 and O-mesitylenesulfonyl-hydroxylamine.

Melting point: 108°–109° C.
Yield: 77% of theory.

EXAMPLE 32

3,3-Dimethyl-5-[4-(benzyl-sulfoximino)-butoxy]-indolinone-2

This compound was prepared analogous to Example 2 from 3,3-dimethyl-5-[4-(benzyl-sulfinyl)-butoxy]-indolinone-2 and O-mesitylenesulfonyl-hydroxylamine.

Melting point: 98°–99° C.
Yield: 82% of theory.

EXAMPLE 33

3,3-Dimethyl-5-[4-(4-fluorophenyl-sulfoximino)-butoxy]-indolinone-2

This compound was prepared analogous to Example 2 from 3,3-dimethyl-5-[4-(4-fluorophenyl-sulfinyl)-butoxy]-indolinone-2 and O-mesitylenesulfonyl-hydroxylamine.

Melting point: 101°–102° C.
Yield: 90% of theory.

EXAMPLE 34

3,3-Dimethyl-5-[4-(4-chlorophenyl-sulfoximino)-butoxy]-indolinone-2

This compound was prepared analogous to Example 2 from 3,3-dimethyl-5-[4-(4-chlorophenyl-sulfinyl)-butoxy]-O-indolinone-2 and O-mesitylenesulfonyl-hydroxylamine.
Melting point: 136°–137° C.
Yield: 76% of theory.

EXAMPLE 35

3,3-Dimethyl-5-[4-(4-bromophenyl-sulfoximino)-butoxy]-indolinone-2

This compound was prepared analogous to Example 2 from 3,3-dimethyl-5-[4-(4-bromophenyl-sulfinyl)-butoxy]-indolinone-2 and O-mesitylenesulfonyl-hydroxylamine.
Melting point: 160°–161° C.
Yield: 88% of theory.

EXAMPLE 36

3,3-Dimethyl-5-[4-(3,4-dichlorophenyl-sulfoximino)-butoxy]-indolinone-2

This compound was prepared analogous to Example 2 from 3,3-dimethyl-5-[4-(3,4-dichlorophenyl-sulfinyl)-butoxy]-indolinone-2 and O-mesitylenesulfonyl-hydroxylamine.
Melting point: 147°–148° C.
Yield: 68% of theory.

EXAMPLE 37

3,3-Dimethyl-5-[4-(2,5-dichlorophenyl-sulfoximino)-butoxy]-indolinone-2

This compound was prepared analogous to Example 2 from 3,3-dimethyl-5-[4-(2,5-dichlorophenyl-sulfinyl)-butoxy]-indolinone-2 and O-mesitylenesulfonyl-hydroxylamine.
$R_f$ value: 0.3 (silicagel plate; eluant: ethyl acetate/methylene chloride 1:1).
Yield: 18% of theory.

EXAMPLE 38

3,3-Dimethyl-5-[4-(3-methyl-4-bromophenyl-sulfoximino)-butoxy]-indolinone-2

This compound was prepared analogous to Example 2 from 3,3-dimethyl-5-[4-(3-methyl-4-bromophenyl-sulfinyl)-butoxy]-indolinone-2 and O-mesitylenesulfonyl-hydroxylamine.
Melting point: 131°–132° C.
Yield: 84% of theory.

EXAMPLE 39

3,3-Dimethyl-5-[4-(2'-fluoro-4-biphenylyl-sulfoximino)-butoxy]-indolinone-2

This compound was prepared analogous to Example 2 from 3,3-dimethyl-5-[4-(2'-fluoro-4-biphenylyl-sulfinyl)-butoxy]-indolinone-2 and O-mesitylenesulfonyl-hydroxylamine.
Melting point: 177°–178° C.
Yield: 90% of theory.

EXAMPLE 40

3,3-Dimethyl-5-[4-(3,5-dibromo-4-aminophenyl-sulfoximino-)-butoxy]-indolinone-2

This compound was prepared analogous to Example 2 from 3,3-dimethyl-5-[4-(3,5-dibromo-4-aminophenyl-sulfinyl)-butoxy]-indolinone-2 and O-mesitylenesulfonyl-hydroxylamine.
Melting point: 202°–204° C.
Yield: 76% of theory.

EXAMPLE 41

3,3-Dimethyl-5-[4-(4-methoxyphenyl-sulfoximino)-butoxy]-indolinone-2

This compound was prepared analogous to Example 2 from 3,3-dimethyl-5-[4-(4-methoxyphenyl-sulfinyl)-butoxy]-indolinone-2 and O-mesitylenesulfonyl-hydroxylamine.
Melting point: 140°–141° C.
Yield: 71% of theory.

EXAMPLE 42

3,3-Dimethyl-5-[4-(2-methoxyphenyl-sulfoximino)-butoxy]-indolinone-2

This compound was prepared analogous to Example 2 from 3,3-dimethyl-5-[4-(2-methoxyphenyl-sulfinyl)-butoxy]-indolinone-2 and O-mesitylenesulfonyl-hydroxylamine.
Colorless resinous substance.
$R_f$ value: 0.35 (silicagel; eluant: ethylene chloride/ethanol=9:1).
Yield: 52% of theory.

EXAMPLE 43

3,3-Dimethyl-5-[4-(3,4-dimethoxyphenyl-sulfoximino)-butoxy]-indolinone-2

This compound was prepared analogous to Example 2 from 3,3-dimethyl-5-[4-(3,4-dimethoxyphenyl-sulfinyl)-butoxy]-indolinone-2 and O-mesitylenesulfonyl-hydroxyamine.
Melting point: 108°–109° C.
Yield: 79% of theory.

EXAMPLE 44

3,3-Dimethyl-5-[4-(6-methoxy-naphth-2-yl-sulfoximino)-butoxy]-indolinone-2

This compound was prepared analogous to Example 2 from 3,3-dimethyl-5-[4-(6-methoxy-naphth-2-yl-sulfinyl)-butoxy]-indolinone-2 and O-mesitylenesulfonyl-hydroxylamine.
Melting point: 174°–175° C.
Yield: 88% of theory.

EXAMPLE 45

6-(4-Methylsulfoximino-butoxy)-3,4-dihydrocarbostyril-mesitylenesulfonate

This compound was prepared analogous to Example 2 from 6-(4-methylsulfinyl-butoxy)-3,4-dihydrocarbostyril and O-mesitylenesulfonyl-hydroxylamine.
Melting point: 130°–133° C.
Yield: 87% of theory.

EXAMPLE 46

3,3-Dimethyl-5-(4-phenylsulfoximino-butoxy)indolinone-2

This compound was prepared analogous to Example 2 from 3,3-dimethyl-5-(4-phenylsulfinyl-butoxy)-indolinone-2 and O-mesitylenesulfonyl-hydroxylamine.
Melting point: 111°–112° C.
Yield: 86% of theory.

EXAMPLE 47

6-[4-(N-Acetyl-3,4-dichlorophenyl sulfoximino)-butoxy]-3,4-dihydrocarbostyril 1.40 gm of 6-[4-(3,4-dichlorophenyl-sulfoximino)-butoxy]-3,4-dihydrocarbostyril were suspended in a mixture of 70 ml of glacial acetic acid and 70 ml of acetic anhydride, and the suspension was stirred for 2½ hours. The solution thus formed was mixed with 300 ml of ice-cold water, while thorough stirring was continued. After 10 minutes, white crystals began to precipitate. After one hour the solution was suction-filtered, and the filter cake was washed with water and crystallized from 140 ml of ethanol in the presence of a little activated charcoal. A white crystalline substance was obtained which was dried in a circulating air drier at 80° C.
Melting point: 150°–152° C.
Yield: 12.9 gm (84% of theory).

EXAMPLE 48

6-[4-(N-Carbamoyl-3,4-dichlorophenyl-sulfoximino)-butoxy]-3,4-dihydrocarbostyril 1.49 gm (0.0035 mol) of 6-[4-(3,4-dichloro-phenylsulfoximino)-butoxy]-3,4-dihydrocarbostyril were dissolved in 70 ml of glacial acetic acid, then 2.8 gm (0.035 mol) of potassium cyanate were added, and the mixture was stirred for 3 hours at room temperature. Then, 40 ml of water are added, while stirring, and the oil which initially precipitated crystallized. It was suction-filtered off, recrystallized from 65 ml of ethanol, and the white crystalline substance was dried at 50° C. in a circulating air drier.
Melting point: 148°–150° C.
Yield: 1.2 gm (70% of theory).

EXAMPLE 49

6-[4-(N-Butyryl-3,4-dichlorophenyl-sulfoximino)-butoxy]-3,4-dihydrocarbostyril 3.0 gm (0.007 mol) of 6-[4-(3,4-dichlorophenyl-sulfoximino)-butoxy]-3,4-dihydrocarbostyril were suspended in 15 ml of pyridine, and 0.9 gm (1.2×0.007 mol) of n-butyric acid chloride was added. A light yellow solution was formed as the mixture was heated to 40° C. After standing for 90 minutes, the mixture was evaporated to dryness in a water aspirator vacuum, using a rotary evaporator, and the residue was taken up in methylene chloride and extracted by shaking twice with 0.5N hydrochloric acid and once with water. After drying over magnesium sulfate, the solvent was distilled off using a rotary evaporator, and the residue was recrystallized from 15 ml of ethanol. Colorless crystals were obtained.
Melting point: 133°–135° C.
Yield: 2.4 gm (69% of theory).

EXAMPLE 50

6-[4-(N-Pivaloyl-3,4-dichlorophenyl-sulfoximino)-butoxy]-3,4-dihydrocarbostyril

This compound was prepared analogous to Example 49, from 6-[4-(3,4-dichlorophenyl-sulfoximino)-butoxy]-3,4-dihydrocarbostyril and pivalic acid chloride.
Melting point: 158°–160° C.
Yield: 81% of theory.

EXAMPLE 51

6-[4-(N-{2-Methoxyacetyl}-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and 2-methoxyacetyl chloride.
Melting point: 103°–105° C.
Yield: 50% of theory.

EXAMPLE 52

6-[4-(N-benzoyl-3,4-dichlorophenyl-sulfoximino)-butoxy]-3,4-dihydrocarbostyril

This compound was prepared analogous to Example 49 from 6-[4-(3,4-dichlorophenyl-sulfoximino)-butoxy]-3,4-dihydrocarbostyril and benzoyl chloride.
Melting point: 110°–111° C.
Yield: 68% of theory.

EXAMPLE 53

6-[4-(N-4-Methoxybenzoyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and 4-methoxybenzoyl chloride.
Melting point: 186°–188° C.
Yield: 70% of theory.

EXAMPLE 54

6-[4-(N-Nicotinoyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and nicotinic acid chloride hydrochloride.
Melting point: 101°–103° C.
Yield: 94% of theory.

EXAMPLE 55

6-[4-(N-{4-methylphenyl-sulfonyl}-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and p-toluenesulfochloride.
Melting point: 154°–156° C.
Yield: 84% of theory.

EXAMPLE 56

6-[4-(N-{2-acetoxyphenyl-acetyl}-3,4-dichlorophenyl-sulfoximino)-butoxy]-3,4-dihydrocarbostyril This compound was prepared from 6-[4-(3,4-dichlorophenyl-sulfoximino)-butoxy]-3,4-dihydrocarbostyril and o-acetyl-D, L-mandelic acid chloride analogous to Example 49. After purification on a silicagel column with ethylene chloride, the compound was obtained as a non-crystallizing glassy resin.

EXAMPLE 57

5-[4-(N-acetyl-3,4-dichlorophenyl-sulfoximino)-butoxy]-3,3-dimethyl-indolinone-2

This compound was prepared analogous to Example 47 from 5-[4-(3,4-dichlorophenyl-sulfoximino)-butoxy]-3,3-dimethyl-indolinone-2 and acetic acid anhydride.
Melting point: 145°–146° C.
Yield: 64% of theory.

EXAMPLE 58

5-[4-(N-butyryl-3,4-dichlorophenyl-sulfoximino)-butoxy]-3,3-dimethyl-indolinone-2

This compound was prepared analogous to Example 49 from 5-[4-(3,4-dichlorophenyl-sulfoximino)-butoxy]-3,3-dimethyl-indolinone-2 and butyric acid chloride.
Melting point: 120°–122° C.
Yield: 81% of theory.

EXAMPLE 59

5-[4-(N-{2-Methoxy-acetyl}-3,4-dichlorophenyl-sulfoximino)-butoxy]-indolinone-2

This compound was prepared analogous to Example 49 from 3,3-dimethyl-5-[4-(3,4-dichlorophenyl-sulfoximino)-butoxy]-indolinone-2 and 2-methoxy-acetyl chloride.
Melting point: 126°–128° C.
Yield: 72% of theory.

EXAMPLE 60

5-[4-(N-Ethoxycarbonyl-3,4-dichlorophenyl-sulfoximino)-butoxy]-3,3-dimethyl-indolinone-2

This compound was prepared analogous to Example 49 from 5-[4-(4-chlorophenyl-sulfoximino)-butoxy]-3,3-dimethyl-indolinone-2 and ethyl chlorocarbonate.
Melting point: 102°–104° C.
Yield: 79% of theory.

EXAMPLE 61

5-[4-(N-Acetyl-4-chlorophenyl-sulfoximino)-butoxy]-3,3-dimethyl-indolinone-2

This compound was prepared analogous to Example 47 from 5-[4-(4-chlorophenyl-sulfoximino)-butoxy]-3,3-dimethyl- indolinone-2 and acetic acid anhydride.
Melting point: 138°–140° C.
Yield: 75% of theory.

EXAMPLE 62

5-[4-(N-Butyryl-4-chlorophenyl-sulfoximino)-butoxy]-3,3-dimethyl-indolinone-2

This compound was prepared analogous to Example 49 from 5-[4-(4-chlorophenyl-sulfoximino)-butoxy]-3,3-dimethyl-indolinone-2 and butyric acid chloride.
Melting point: 166°–168° C.
Yield: 38% of theory.

EXAMPLE 63

5-[4-(N-Pivaloyl-4-chlorophenyl-sulfoximino)-butoxy]-3,3-dimethyl-indolinone-2

This compound was prepared analogous to Example 49 from 5-[4-(4-chlorophenyl-sulfoximino) butoxy]-3,3-dimethyl indolinone-2 and pivalic acid chloride.
Melting point: 95°–97° C.
$R_f$ value: 0.2 (silicagel plate, ethylene chloride).
Yield: 50% of theory.

Yield: 76% of theory.

EXAMPLE 64

5-[4-(N-caproyl-4-chlorophenyl-sulfoximino)-butoxy]-3,3-dimethyl-indolinone-2

This compound was prepared analogous to Example 49 from 5-[4-chlorophenyl-sulfoximino)-butoxy]-3,3-dimethyl-indolinone-2 and caprylic acid chloride.
Resin.
$R_f$ value: 0.5 (silicagel plate, ethyl acetate/methylene chloride=1:1).
Yield: 95% of theory.

EXAMPLE 65

5-[4-(N-carbamoyl-4-chlorophenyl-sulfoximino)-butoxy]-3,3-dimethyl-indolinone-2

This compound was prepared analogous to Example 48 from 5-[4-(4-chlorophenyl-sulfoximino)-butoxy]-3,3-dimethyl- indolinone-2 and potassium cyanate.
Colorless resin.
$R_f$ value: 0.4 (silicagel plate, ethylene chloride/ethanol=9:1).
Yield: 75% of theory

EXAMPLE 66

5-[4-(N-Dimethylaminocarbonyl-4-chlorophenyl-sulfoximino)-butoxy]-3,3-dimethyl-indolinone-2

This compound was prepared analogous to Example 49 from 5-[4-(4-chlorophenyl-sulfoximino)-butoxy]-3,3-dimethyl-indolinone-2 and dimethylcarbamoyl chloride.
Melting point: 170°–172° C.
Yield: 64% of theory.

EXAMPLE 67

6-[4-(N-Acetyl-3,4-dimethoxyphenyl-sulfoximino)-butoxy]-3,4-dihydrocarbostyril

This compound was prepared analogous to Example 47 from 6-[4-(3,4-dimethoxyphenyl-sulfoximino)-butoxy]-3,4-dihydrocarbostyril and acetic acid anhydride.
Melting point: 89°–92° C.
Yield: 60% of theory.

EXAMPLE 68

6-[4-(N-Butyryl-3,4-dimethoxyphenyl-sulfoximino)-butoxy]-3,4-dihydrocarbostyril

This compound was prepared analogous to Example 49 from 6-[4-(3,4-dimethoxyphenyl-sulfoximino)-butoxy]-3,4-dihydrocarbostyril and butyric acid chloride.
Glassy colorless resin.
$R_f$ value: 0.35 (silicagel plate, ethylene chloride/ethanol=9:1).
Yield: 41% of theory.

EXAMPLE 69

6-[4-(N-Benzoyl-3,4-dimethoxyphenyl-sulfoximino)-butoxy]-3,4-dihydrocarbostyril

This compound was prepared analogous to Example 49 from 6-[4-(3,4-dimethoxyphenyl-sulfoximino)-butoxy]-3,4-dihydrocarbostyril and benzoyl chloride.
Melting point: 78°–80° C.
Yield: 50% of theory.

EXAMPLE 70

6-[4-(N-{4-Chlorobenzoyl}-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4-dihydrocarbostyril and 4-chloro-benzoyl chloride.
Melting point: 134°–137° C.
Yield: 61% of theory.

EXAMPLE 71

6-[4-(N-{4-tert.Butyl-benzoyl}-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4-dihydrocarbostyril and 4-tert. butyl-benzoyl chloride.
Melting point: 98°–101° C.
Yield: 87% of theory.

EXAMPLE 72

6-[4-(N-Nicotinoyl-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4-dihydrocarbostyril and nicotinic acid chloride hydrochloride.
Melting point: 90°–93° C.
Yield: 75% of theory

EXAMPLE 73

6-[4-(N-Pentamethylphenylsulfonyl-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4- dihydrocarbostyril and pentamethylbenzene-sulfonic acid chloride.
Melting point: 186°–188° C.
Yield: 75% of theory.

EXAMPLE 74

5-[4-(N-acetyl-3,4-dimethoxyphenyl-sulfoximino)-butoxy]-3,3-dimethylindolin-2one This compound was prepared analogous to Example 47 from 5-[4-(3,4-dimethoxyphenyl-sulfoximino)-butoxy]-3,3-dimethyl-indolin-2-one and acetic acid anhydride.
Glassy resin.
$R_f$ value: 0.3 (silicagel plate, ethylene chloride/ethanol=9:1).
Yield: 99% of theory.

EXAMPLE 75

5-[4-(N-butyryl-3,4-dimethoxyphenyl-sulfoximino)-butoxy]-3,3-dimethyl-indolin-2-one This compound was prepared analogous to Example 49 from 5-[4-(3,4-dimethoxyphenyl-sulfoximino)-butoxy]-3,3-dimethyl-indolin-2-one and butyric acid chloride.
Resin.
$R_f$ value: 0.35 (silicagel plate, ethyl acetate/methylene chloride=1:1).
Yield: 92% of theory.

EXAMPLE 76

5-[4-(N-pivaloyl-3,4-dimethoxyphenyl-sulfoximino)-butoxy]-3,3-dimethyl-indolinone-2

This compound was prepared analogous to Example 49 from 5-[4-(3,4-dimethoxyphenyl-sulfoximino)-butoxy]-3,3-dimethyl-indilinone-2 and pivalic acid chloride.
Resin.
$R_f$ value: 0.45 (silicagel plate, ethyl acetate/methylene chloride=1:1).
Yield: 88% of theory.

EXAMPLE 77

5-[4-(N-Carbamoyl-3,4-dimethoxyphenyl-sulfoximino)-butoxy]-3,3-dimethyl-indolinone-2

This compound was prepared analogous to Example 48 from 5-[4-(3,4-dimethoxyphenyl-sulfoximino)-butoxy]-3,3-dimethyl-indolinone-2 and potassium cyanate.
Resin.
$R_f$ value: 0.25 (silicagel plate, ethylene chloride/ethanol=9:1).
Yield: 75% of theory.

EXAMPLE 78

5-[4-(N-Dimethylaminocarbonyl-3,4-dimethoxyphenyl-sulfoximino)-butoxy]-3,3-dimethyl-indolinone-2

This compound was prepared analogous to Example 49 from 5-[4-(3,4-dimethoxyphenyl-sulfoximino)-butoxy]-3,3-dimethyl-indolinone-2 and dimethylcarbamoyl chloride.
Resin.
$R_f$ value: 0.3 (silicagel plate, ethylene chloride/ethanol=9:1).
Yield 98% of theory.

EXAMPLE 79

5-[4-(N-4-Chloro-benzoyl)-3,4-dimethoxyphenyl-sulfoximino)-butoxy]-3,3-dimethyl-indolinone-2

This compound was prepared analogous to Example 49 from 5-[4-(3,4 dimethoxyphenyl-sulfoximino)-butoxy]-3,3-dimethyl-indolinone-2 and 4-chloro-benzoyl chloride.
Melting point: 174°–177° C.
Yield: 74% of theory.

EXAMPLE 80

5-[4-(N-Nicotinoyl-3,4-dimethoxyphenyl-sulfoximino)-butoxy]-3,3-dimethyl-indolinone-2

This compound was prepared analogous to Example 49 from 5-[4-(3,4-dimethoxyphenyl-sulfoximino)-butoxy]-3,3-dimethyl-indolinone-2 and nicotinic acid chloride hydrochloride.
Resin.
$R_f$ value: 0.25 (silicagel plate, ethylene chloride/ethanol=9:1).
Yield: 76% of theory.

EXAMPLE 81

6-[4-(N-{2-Naphthoyl}-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4-dihydrocarbostyril and 2-naphthoic acid chloride.
Resin.

R$_f$ value: 0.45 (silicagel plate, ethyl acetate/methylene chloride=1:1).
Yield: 93% of theory.

EXAMPLE 82

6-[4-(N-{1-Naphthoyl}-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4-dihydrocarbostyril and 1-naphthoic acid chloride.

Resin.

R$_f$ value: 0.3 (silicagel plate, ethyl acetate/methylene chloride=1:1).
Yield: 83% of theory.

EXAMPLE 83

6-[4-(N-{2-Thienoyl}-3,4-dimethoxyphenyl-sulfoximino)-butoxy]-3,4-dihydrocarbostyril This compound was prepared analogous to Example 49 from 6-[4-(3,4-dimethoxyphenyl-sulfoximino)-butoxy]-3,4-dihydrocarbostyril and thiophene-2-carboxylic acid chloride.

Resin.

R$_f$ value: 0.3 (silicagel plate, ethyl acetate/methylene chloride=1:1).
Yield: 88% of theory.

EXAMPLE 84

6-[4-(3,4-Dimethoxyphenyl-sulfoximino)-butoxy]-3,4-dihydrocarbostyril

This compound was prepared analogous to Example 2 from 6-[4-(3,4-dimethoxyphenyl-sulfinyl)-butoxy]-3,4-dihydrocarbostyril and O-mesitylenesulfonyl-hydroxylamine.

Melting point: 154°–156° C.
Yield: 64% of theory.

EXAMPLE 85

6-[4-(N-Benzoyl-4-fluorophenyl-sulfoximino)-butoxy]-3,4-dihydrocarbostyril

This compound was prepared analogous to Example 49 from 6-[4-(4-fluorophenyl-sulfoximino)-butoxy]-3,4-dihydrocarbostyril and benzoyl chloride.

Melting point: 64°–68° C.
Yield: 87% of theory.

EXAMPLE 86

6-[4-(N-{4-chloro-benzoyl}-4-fluorophenyl-sulfoximino)-butoxy]-3,4-dihydrocarbostyril This compound was prepared analogous to Example 49 from 6-[4-fluorophenyl-sulfoximino)-butoxy]-3,4-dihydrocarbostyril and 4-chloro-benzoyl chloride.

Melting point: 134°–138° C.
Yield: 78% of theory.

EXAMPLE 87

6-[4-(3,4-Dichlorophenyl-sulfoximino)-butoxy]-3,4-dihydrocarbostyril 145.5 gm of p-toluenesulfonic acid were dissolved in 350 ml of dimethylformamide, while stirring, and 70.1 gm of 6-[4-(3,4-dichlorophenyl-sulfinyl)-butoxy]-3,4-dihydrocarbostyril were stirred in. Then, 106.7 gm of ethyl O-mesitylenesulfonyl-hydroxamate were added. The reaction was slightly exothermic, and the reaction mixture was occasionally cooled to ensure that the temperature did not exceed 20° C. After 46 hours, 350 ml of water were introduced, while thoroughly stirring, until the first slight turbidity appeared. After the addition of a suspension of seed crystals, crystallization of a large proportion of the product began over a period of 30 minutes, while stirring was continued. To complete crystallization, an additional 300 ml of water were stirred in. The mixture was stirred for another 30 minutes, and then the crystals of the salt of O-mesitylenesulfonic acid thus formed were suction-filtered off and washed with water. The filter cake, while still wet with water, was suspended in 500 ml of methanol, and 100 ml of 2N sodium hydroxide were stirred in all at once. The substance briefly went into solution, but then crystallization of the free sulfoximine occurred. The mixture was stirred for half an hour more at room temperature suction-filtered, and the filter cake was washed with ice-cold methanol. The product was dried at 80° C. in a circulating air drier.

Melting point: 160°–162° C.
Yield: 61.7 gm (84.9% of theory).

EXAMPLE 88

6-[4-(3,4-dichlorophenyl-N-{4-toluenesulfonyl}-sulfoximino)-butoxy]-3,4-dihydrocarbostyril 200 mg of 6-[4-(3,4-dichlorophenyl-N-{4-toluenesulfonyl}-sulfimino)-butoxy]-3,4-dihydrocarbostyril, prepared from 6-[4-(3,4-dichlorophenyl-mercapto)-butoxy]-3,4-dihydrocarbostyril and N-chloro-4-toluenesulfonamide sodium (Chloramine T), were suspended in methanol, 0.35 ml of 2N sodium hydroxide and 0.06 ml of hydrogen peroxide solution (397.4 mg/ml) were added, and the resulting mixture was refluxed for 4 hours. As it began to boil, a clear solution was formed and after one hour crystals were precipitated. After further heating, the crystals were suction-filtered off while still hot and dried in the air.

Melting point: 155°–157° C.
Yield: 59% of theory.

EXAMPLE 89

6-[3-(3,4-Dichlorophenyl-sulfoximino)-propoxy]-3,4-dihydrocarbostyril

This compound was prepared analogous to Example 2 from 6-[3-(3,4-dichlorophenyl-sulfinyl)-propoxy]-3,4-dihydrocarbostyril and O-mesitylenesulfonyl-hydroxylamine.

Melting point: 144°–146° C.
Yield: 67% of theory.

EXAMPLE 90

6-[5-(3,4-dichlorophenyl-sulfoximino)-pentoxy]-3,4-dihydrocarbostyril

This compound was prepared analogous to Example 2 from 6-[5-(3,4-dichlorophenyl-sulfinyl)-pentoxy]-3,4-dihydrocarbostyril and O-mesitylenesulfonyl-hydroxylamine.

Melting point: 154°–155° C.
Yield: 29% of theory

EXAMPLE 91

6-(3-Ethylsulfoximino-propoxy)-3,4-dihydrocarbostyril

This compound was prepared analogous to Example 2 from 6-(3-ethylsulfinyl-propoxy)-3,4-dihydrocarbostyril and O-mesitylenesulfonyl-hydroxylamine.

Melting point: 107°–109° C.

Yield: 61% of theory.

EXAMPLE 92

6-[4-(N-4-cyanobenzoyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and 4-cyano-benzoyl chloride.
Melting point: 200°–202° C.
Yield: 79% of theory.

EXAMPLE 93

6-[4-(N-2-Thienoyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and 2-thiophene carboxylic acid chloride.
Melting point: 100°–102° C.
Yield: 61% of theory.

EXAMPLE 94

6-[4-N-(+)-Pinanoyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and (+)-pinanic acid chloride.
Melting point: 69°–74° C.
Yield: 94% of theory.

EXAMPLE 95

6-[4-(N-(−)-Pinanoyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and (−)-pinanic acid chloride.
Melting point: 69°–74° C.
Yield: 91% of theory.

EXAMPLE 96

6-[4-(N-{Pentamethylphenyl-sulfonyl}-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and pentamethylphenyl sulfochloride.
Melting point: 149°–151° C.
Yield: 83% of theory.

EXAMPLE 97

6-[4-(N-Methanesulfonyl-3,4-dichlorophenyl-sulfoximino)-butoxy]-3,4-dihydrocarbostyril This compound was prepared analogous to Example 49 from 6-[4-(3,4-dichlorophenyl-sulfoximino)-butoxy]-3,4-dihydrocarbostyril and methanesulfonyl chloride.
Melting point: 172°–174° C.
Yield: 37% of theory

EXAMPLE 98

6-[4-(N-Acetyl-4-cyclohexylphenyl-sulfoximino)-butoxy]-3,4-dihydrocarbostyril

This compound was prepared analogous to Example 47 from 6-[4-(4-cyclohexylphenyl-sulfoximino)-butoxy]-3,4-dihydrocarbostyril and acetic acid anhydride.
Melting point: 135°–136° C.
Yield: 92% of theory.

EXAMPLE 99

6-[4-(N-Pivaloyl-4-cyclohexylphenyl-sulfoximino)-butoxy]-3,4-dihydrocarbostyril

This compound was prepared analogous to Example 49 from 6-[4-(4-cyclohexylphenyl-sulfoximino)-butoxy]-3,4-dihydrocarbostyril and pivaloyl chloride.
Melting point: 170°–172° C.
Yield: 95% of theory.

EXAMPLE 100

6-[4-(N-Benzoyl-4-cyclohexylphenyl-sulfoximino)-butoxy]-3,4-dihydrocarbostyril

This compound was prepared analogous to Example 49 from 6-[4-(4-cyclohexylphenyl-sulfoximino)butoxy]-3,4-dihydrocarbostyril and benzoyl chloride.
Melting point: 187°–189° C.
Yield: 92% of theory.

EXAMPLE 101

6-[4-(N-Acetyl-4-fluorophenyl-sulfoximino)-butoxy]-3,4-dihydrocarbostyril

This compound was prepared analogous to Example 47 from 6-[4-(4-fluorophenyl-sulfoximino)-butoxy]-3,4-dihydrocarbostyril ($R_f$ value: 0.60) and acetic acid anhydride.
$R_f$ value: 0.65 (silicagel; eluant: ethylene chloride/ethanol = 85:15).
Yield: 54% of theory.

EXAMPLE 102

6-[4-(N-Butyroyl-4-fluorophenyl-sulfoximino)-butoxy]-3,4-dihydrocarbostyril

This compound was prepared analogous to Example 49 from 6-[4-(4-fluorophenyl-sulfoximino)-butoxy]-3,4-dihydrocarbostyril ($R_f$ value: 0.60) and butyric acid chloride.
$R_f$ value: 0.70 (silicagel; eluant: ethylene chloride/ethanol = 85:15).
Yield: 78% of theory.

EXAMPLE 103

6-[4-(N-2-Methoxyacetyl-4-fluorophenyl-sulfoximino)-butoxy]-3,4-dihydrocarbostyril This compound was prepared analogous to Example 49 from 6-[4-(4-fluorophenyl-sulfoximino)-butoxy]-3,4-dihydrocarbostyril ($R_f$ value: 0.60) and 2-methoxyacetyl chloride.
$R_f$ value: 0.66 (silicagel; eluant: ethylene chloride/ethanol = 85:15).
Yield: 67% of theory.

EXAMPLE 104

6-[4-(N-(+)-Pinanoyl-4-fluorophenyl-sulfoximino)-butoxy]-3,4 dihydrocarbostyril

This compound was prepared from 6-[4-(4-fluorophenyl-sulfoximino)-butoxy]-3,4-dihydrocarbostyril and (+)-pinanic acid chloride analogous to Example 49.
Melting point: 116°–120° C.
Yield: 61% of theory.

EXAMPLE 105

6-[4-(N-(−)-Pinanoyl-4-fluorophenyl-sulfoximino)-butoxy]-3,4-dihydrocarbostyril

This compound was prepared analogous to Example 49 from 6-[4-(4-fluorophenyl-sulfoximino)-butoxy]-3,4-dihydrocarbostyril and (−)-pinanic acid chloride.
Melting point: 122°–123° C.
Yield: 45% of theory.

EXAMPLE 106

6-[4-(N-4-Toluenesulfonyl-4-fluorophenyl-sulfoximino)-butoxy]-3,4-dihydrocarbostyril This compound was prepared analogous to Example 49 from 6-[4-(4-fluorophenyl-sulfoximino)-butoxy]-3,4-dihydrocarbostyril and 4-toluenesulfochloride.
Melting point: 67°–70° C.
Yield: 57% of theory.

EXAMPLE 107

6-[4-(N(+)-10-Camphorsulfonyl-4-fluorophenyl-sulfoximino)-butoxy]-3,4-dihydrocarbostyril This compound was prepared analogous to Example 49 from 6-[4-(4-fluorophenyl-sulfoximino)-butoxy]-3,4-dihydrocarbostyril and (+)-10-camphorsulfochloride.
Melting point: 81°–100° C.
Yield: 61% of theory.

EXAMPLE 108

6-[4-(N-4-Chlorobenzoyl-methylsulfoximino)-butoxy]-3,4-dihydrocarbostyril

This compound was prepared analogous to Example 49 from 6-(4-methylsulfoximino-butoxy -3,4-dihydrocarbostyril and 4-chlorobenzoyl chloride.
Melting point: 176°–178° C.
Yield: 87% of theory.

EXAMPLE 109

6-(4-n-Hexylsulfoximino-butoxy)-3,4-dihydrocarbostyril

This compound was prepared analogous to Example 2 from 6-(4-n-hexylsulfinyl-butoxy)-3,4-dihydrocarbostyril and O-mesitylenesulfonyl-hydroxylamine.
Melting point: 111°–113° C.
Yield: 59% of theory.

EXAMPLE 110

6-(N-Acetyl-4-n-hexylsulfoximino-butoxy)-3,4-dihydrocarbostyril

This compound was prepared analogous to Example 47 from 6-(4-n-hexylsulfoximino-butoxy)-3,4-dihydrocarbostyril and acetic acid anhydride.
Melting point: 119°–121° C.
Yield: 90% of theory.

EXAMPLE 111

6-(N-Benzoyl-4-n-hexylsulfoximino-butoxy)-3,4-dihydrocarbostyril

This compound was prepared analogous to Example 49 from 6-(4-n-hexylsulfoximino-butoxy)-3,4-dihydrocarbostyril and benzoyl chloride.
Melting point: 112°–114° C.
Yield: 75% of theory.

EXAMPLE 112

6-[4-(2-Phenylethyl-sulfoximino)-butoxy]-3,4-dihydrocarbostyril

This compound was prepared analogous to Example 2 from 6-[4-(2-phenylethyl-sulfinyl)-butoxy]-3,4-dihydrocarbostyril and O-mesitylenesulfonyl-hydroxylamine.
Melting point: 158°–159° C.
Yield: 69% of theory.

EXAMPLE 113

5-(4-Phenylsulfoximino-butoxy)-3,4-dihydrocarbostyril

This compound was prepared analogous to Example 2 from 5-(4-phenylsulfinyl-butoxy)-3,4-dihydrocarbostyril and O-mesitylenesulfonyl-hydroxylamine.
Melting point: 159°–160° C.
Yield: 76% of theory.

EXAMPLE 114

5-(N-Acetyl-4-phenylsulfoximino-butoxy)-3,4-dihydrocarbostyril

This compound was prepared analogous to Example 47 from 5-(4-phenylsulfoximino-butoxy)-3,4-dihydrocarbostyril and acetic acid anhydride.
Melting point: 134°–137° C.
Yield: 61% of theory.

EXAMPLE 115

7-(4-Phenylsulfoximino-butoxy) 3,4-dihydrocarbostyril

This compound was prepared analogous to Example 87 from 7-(4-phenylsulfinyl-butoxy)-3,4-dihydrocarbostyril, ethyl o-mesitylenesulfonyl-hydroxamate and p-toluenesulfonic acid.
Melting point: 137°–139° C.
Yield: 81% of theory.

EXAMPLE 116

7-(N-Acetyl-4-phenylsulfoximino-butoxy)-3,4-dihydrocarbostyril

This compound was prepared analogous to Example 47 from 7-(4-phenylsulfoximino-butoxy)-3,4-dihydrocarbostyril and acetic acid anhydride.
Melting point: 111°–113° C.
Yield: 78% of theory.

EXAMPLE 117

8-(4-Phenylsulfoximino-butoxy)-3,4-dihydrocarbostyril

This compound was prepared analogous to Example 2 from 8-(4-phenylsulfinyl-butoxy)-3,4-dihydrocarbostyril and O-mesitylenesulfonyl-hydroxylamine.
Melting point: 78°–80° C.
Yield: 96% of theory.

EXAMPLE 118

8-(N-Acetyl-4-phenylsulfoximino-butoxy)-3,4-dihydrocarbostyril

This compound was prepared analogous to Example 47 from 8-(4-phenylsulfoximino-butoxy)-3,4-dihydrocarbostyril and acetic acid anhydride.
Melting point: 116°–118° C.
Yield: 82% of theory.

EXAMPLE 119

6-(3-Ethylsulfoximino-propoxy)-carbostyril

This compound was prepared analogous to Example 2 from 6-(3-ethylsulfinyl-propoxy)-carbostyril and O-mesitylenesulfonyl-hydroxylamine.
Melting point: 116°–117° C.
Yield: 80% of theory.

EXAMPLE 120

6-[4-(N-Benzoyl-4-fluorophenyl-sulfoximino)-butoxy]-carbostyril

This compound was prepared analogous to Example 49 from 6-[4-(4-fluorophenyl-sulfoximino)-butoxy]-carbostyril and benzoyl chloride.
Melting point: 137°–141° C.
Yield: 34% of theory.

EXAMPLE 121

3,3-Dimethyl-5-[4-(3,4-dimethylphenyl-sulfoximino)-butoxy]-indolinone-2

This compound was prepared analogous to Example 87 from 3,3-dimethyl 5-[4-(3,4-dimethylphenyl-sulfinyl)-butoxy]-indolinone-2, ethyl O-mesitylenesulfonyl-hydroxamate and p-toluenesulfonic acid.
Melting point: 153°–154° C.
Yield: 77% of theory.

EXAMPLE 122

3,3-Dimethyl-5-[4-(N-acetyl-3,4-dimethylphenyl-sulfoximino)-butoxy]-indolinone-2

This compound was prepared analogous to Example 47 from 3,3-dimethyl-5-[4-(3,4-dimethylphenyl-sulfoximino)-butoxy]-indolinone-2 and acetic acid anhydride.
Melting point: 150°–152° C.
Yield: 78% of theory.

EXAMPLE 123

3,3-Dimethyl-5-(4-methylsulfoximino-butoxy)-indolinone-2

This compound was prepared analogous to Example 2 from 3,3-dimethyl-5-(4-methylsulfinyl-butoxy)-indolinone-2 and O-mesitylenesulfonyl-hydroxylamine.
Melting point: 123°–124° C.
Yield: 98% of theory.

EXAMPLE 124

3,3-Dimethyl-5-[4-(N-4-chlorophenylaminocarbonyl-methylsulfoximino)-butoxy]-indolinone-2

This compound was prepared from 3,3-dimethyl-5-(4-methylsulfoximino-butoxy)-indolinone-2 and 4-chlorophenyl isocyanate by stirring in absolute dioxane at room temperature for 30 minutes analogous to Example 48.
Melting point: 175°–177° C.
Yield: 89% of theory.

EXAMPLE 125

3,3-Dimethyl-5-[4(N-4-toluenesulfonyl-4-methylsulfoximino)-butoxy]-indolinone-2

This compound was prepared analogous to Example 49 from 3,3-dimethyl-5-(4-methylsulfoximino-butoxy)-indolinone-2.
$R_f$ value: 0.70 (silicagel, eluant: ethyl acetate/methylene chloride = 1:1).
Yield: 63% of theory.

EXAMPLE 126

3,3-Dimethyl-5-[4-(N-4-chlorobenzoyl-methylsulfoximino)-butoxy]-indolinone-2

This compound was prepared analogous to Example 49 from 3,3-dimethyl-5-(4-methylsulfoximino-butoxy)-indolinone-2 and 4-chlorobenzoyl chloride.
Melting point: 176°–178° C.
Yield: 73% of theory.

EXAMPLE 127

6-[4-(N-acetyl-3,4-dichlorophenyl-sulfoximino)-butoxy]-3,4-dihydrocarbostyril 1-(3,4-Dichlorophenyl-sulfinyl)-4-bromo-butane was reacted with O-mesitylenesulfonyl-hydroxylamine analogous to Example 2 to obtain 1-(3,4-dichlorophenyl-sulfoximino)-4-bromo-butane, which was then converted into 1-[3,4-dichlorophenyl-(N-acetyl-sulfoximino)]-4-bromo-butane with acetic acid anhydride analogous to Example 47.
Melting point: 170°–173° C.
Yield: 98% of theory.

A solution of 163.2 mg (0.001 mol) of 6-hydroxycarbostyril in 2 ml of dimethylsulfoxide was mixed with 448 mg (0.0013 mol) of 1-[3,4-dichlorophenyl-(N-acetylsulfoximino)]-4-bromo-butane and 276.4 mg (0.002 mol) of anhydrous potassium carbonate, and the mixture was stirred for 17 hours at room temperature. The reaction mixture was then mixed with water in small portions, whereupon the reaction product crystallized out in the form of white needles.
Melting point: 149°–151° C.
Yield: 267.1 mg (62.5% of theory).

EXAMPLE 128

6-(4-Methylsulfimino-butoxy)-3,4-dihydrocarbostyril hydrogensulfate 0.12 gm of sodium were dissolved in 25 ml of methanol, 1.3 gm of 6-(4-methylmercapto-butoxy)-3,4-dihydrocarbostyril were added to the solution while stirring and, over a period of 40 minutes, 0.57 gm of hydroxylamino-O-sulfonic acid was added at a temperature of 17° C. The temperature rose to 22° C. The mixture was stirred overnight, then the precipitated sodium sulfate was removed by suction filtration and, by the gradual addition of ether, a resinous substance was precipitated which, when triturated with ether, crystallized to form a somewhat hygroscopic substance. This product was suction-filtered off and dried in a vacuum desiccator over calcium chloride.
Melting point: 75°–80° C.
Yield: 0.656 gm (20% of theory).

EXAMPLE 129

6-[4-(3,4-Dichlorophenyl-sulfimino)-butoxy]-3,4-dihydrocarbostyril mesitylenesulfonate This compound was prepared analogous to Example 2 from 6-[4-(3,4-dichlorophenyl-mercapto)-butoxy]-3,4-dihydrocarbostyril and O-mesitylenesulfonyl-hydroxylamine.
Melting point: 82°–83° C.
Yield: 49% of theory.

EXAMPLE 130

6-[4-(3,4-Dimethoxyphenyl-sulfimino)-butoxy]-3,4-dihydrocarbostyril mesitylenesulfonate This compound was prepared analogous to Example 2 from 6-[4-(3,4-dimethoxyphenyl-mercapto)-butoxy]-3,4-dihydrocarbostyril and O-mesitylenesulfonyl-hydroxylamine.

Melting point: 140°–145° C.
Yield 83% of theory.

EXAMPLE 131

6-[4-(2'-Fluoro-4-biphenylyl-sulfimino)-butoxy]-carbostyril mesitylenesulfonate

This compound was prepared analogous to Example 2 from 6-[4-(2'-fluoro-4-biphenylyl-mercapto)-butoxy]-carbostyril and O-mesitylenesulfonyl-hydroxylamine.

Melting point: 125°–128° C.
Yield: 63% of theory.

EXAMPLE 132

6-[4-(4-tert.butylphenyl-sulfimino)-butoxy]-carbostyril

This compound was prepared analogous to Example 2 from 6-[4-(4-tert.butylphenyl-mercapto)-butoxy]-carbostyril and O-mesitylenesulfonyl-hydroxylamine.

Melting point: 145°–150° C.
Yield: 55% of theory.

EXAMPLE 133

6-[4-(N 4-toluenesulfonyl-4-fluorophenyl-sulfimino)-butoxy]-3,4-dihydrocarbostyril 0.70 gm of 6-[4-(4-fluorophenyl-mercapto)-butoxy]-3,4-dihydrocarbostyril were suspended in 20 ml of methanol, and a clear solution of 1.16 gm of N-chloro-4-toluenesulfonamide sodium was added to the suspension. After stirring the mixture overnight at room temperature, the ethanol was distilled off. The residue thus obtained was chromatographed on a silicagel column, using methylene chloride/ethyl acetate (1:1) as the eluant.

Melting point: 122°–124° C.
Yield: 0.59 gm (57% of theory).

EXAMPLE 134

6-[4-(N-4-Toluenesulfonyl-3,4-dichlorophenyl-sulfimino)-butoxy]-3,4-dihydrocarbostyril This compound was prepared analogous to Example 133 from 6-[4-(3,4-dichlorophenyl-mercapto)-butoxy]-3,4-dihydrocarbostyril and N-chloro-4-toluenesulfonylamide sodium.

Melting point: 150°–152° C.
Yield: 62% of theory.

EXAMPLE 135

5-[4-(N-4-Toluenesulfonyl-4-bromophenyl-sulfimino)-butoxy]-3,3-dimethyl-indolinone-2

This compound was prepared analogous to Example 133 from 5-[4-(4-bromophenyl-mercapto)-butoxy]-3,3-dimethyl-indolinone-2 and N-chloro-4-toluenesulfonamide sodium.

Melting point: 163°–164° C.
Yield: 33% of theory.

EXAMPLE 136

6-[4-(N-4-Toluenesulfonyl-methoxyphenylsulfimino)-butoxy]-3,4-dihydrocarbostyril This compound was prepared analogous to Example 133 from 6-[4-(3-methoxyphenyl-mercapto)-butoxy]-3,4-dihydrocarbostyril and N-chloro-4-toluenesulfonamide sodium.

Melting point: 110°–114° C.
Yield: 38% of theory.

EXAMPLE 137

6-[4-(N-4-toluenesulfonyl-phenylsulfimino)-butoxy]-3,4-dihydrocarbostyril

This compound was prepared analogous to Example 133 from 6-(4-phenylmercapto-butoxy)-3,4-dihydrocarbostyril ($R_f$ value=0.45) and N-chloro-4-toluenesulfonamide sodium.

Melting point: 58° C. (sintering).
$R_f$ value: 0.37 (silicagel, ethylene chloride/ethanol=9:1).
Yield: 62% of theory.

EXAMPLE 138

6-[4-(N-4-Toluenesulfonyl-cyclohexylsulfimino)-butoxy]-3,4-dihydrocarbostyril

This compound was prepared analogous to Example 133 from 6-(4-cyclohexylmercapto-butoxy)-3,4-dihydrocarbostyril and N-chloro-4-toluenesulfonamide sodium.

Melting point: 162°–163° C.
Yield: 53% of theory.

EXAMPLE 139

6-[4-(N-4-Toluenesulfonyl-3,4-dichlorophenyl-sulfimino)-butoxy]-carbostyril

This compound was prepared analogous to Example 133 from 6-[4-(3,4-dichlorophenyl-mercapto)-butoxy]-carbostyril ($R_f$ value: 0.34) and N-chloro-4-toluenesulfonamide sodium. $R_f$ value: 0.32 (silicagel plate, ethylene chloride/ethanol=9:1).
Yield: 39% of theory.

The compounds of the present invention, that is, those embraced by formula I above and their non-toxic, pharmacologically acceptable acid addition salts, have useful pharmacodynamic properties. More particularly, they exhibit antithrombotic activity in warm-blooded animals. Antithrombotic activity increases the synthesis of the aggregation-inhibiting prostaglandin $I_2$ (prostacyclin).

In addition, the compounds of the present invention where n is 0 are useful as intermediates for the preparation of compounds of the formula I wherein n is 1.

Furthermore, the compounds of the instant invention have an inhibiting effect on tumor metastasis, which is based on the following properties of the compounds of the invention:

1. They are *platelet phosphodiesterase inhibitors,* which are known to be inhibitors of tumor metastasis [H. Gastpar, Thrombosis Research 5, 277–289 (1974); and K. V. Honn, Science 212, 1270–1272 (1981)].

2. The compounds produce a significant increase in the bleeding time, i.e. they inhibit primary haemostasis, the first aggregation of thrombocytes at the injured blood vessel, to form a pure platelet thrombus, even when administered in very low doses. In the case of the compounds of the formula I this cannot be explained by a limitation of platelet function alone, but must be due to an increased release of prostacyclin from the endothelial cells of the blood vessel. This is confirmed by the fact that the prolongation of bleeding time does not occur if the synthesis of prostacyclin in the endothelial cells is prevented by prior administration of cyclooxygenase inhibitors. Thus, the novel compounds constitute a hitherto unknown optimum combination of two basic effects, namely an increased cAMP level by stimulating production (prostacyclin) and simultaneous inhibition of degradation (PDE inhibition). According to HONN [K. V. Honn, Science 212, 1270–1272 (1981)] the increase in prostacyclin activity or prostacyclin synthesis in the wall of the blood vessel thus observed is also a cause of the inhibition of tumor metastasis.

The above pharmacological properties of the compounds of the present invention were ascertained by the standard test methods described below, and the results of these tests for a few representative species of the genus are shown in the tables, where A = 6-(4-methylsulfoximino-butoxy)-3,4-dihydrocarbostyril mesitylenesulfonate,
B = 6-(4-phenylsulfoximino-butoxy)-3,4-dihydrocarbostyril,
C = 6-[4-(4-fluorophenyl-sulfoximino)-butoxy]-3,4-dihydrocarbostyril,
D = 6-[4-(4-chlorophenyl-sulfoximino)-butoxy]-3 4-dihydrocarbostyril,
E = 6-[4-(N-acetyl-3,4-dichlorophenyl-sulfoximino)-butoxy-3,4-dihydrocarbostyril,
F = 6-[4-(N-p-toluenesulfonyl-3,4-dichlorophenyl-sulfoximino)-butoxy]-3,4-dihydrocarbostyril,
G = 6-[4-(4-fluorophenyl-sulfoximino)-butoxy]-carbostyril,
H = 6-[4-(4-chlorophenyl-sulfoximino)-butoxy]-carbostyril,
I = 6-[4-(3-methyl-4-bromophenyl-sulfoximino)-butoxy]-carbostyril,
K = 6-[4-(4-tert.butylphenyl-sulfoximino)-butoxy]-3,4-dihydrocarbostyril,
L = 6-[4-(4-cyclohexylphenyl-sulfoximino)-butoxy]-3,4-dihydrocarbostyril,
M = 6-[4-(4-tert.butylphenyl-sulfoximino)-butoxy]-carbostyril,
N = 6-(4-cyclohexylsulfoximino-butoxy)-carbostyril,
O = 6-[4-(N-butyryl-3,4-dichlorophenyl-sulfoximino)-butoxy]-3,4-dihydrocarbostyril,
P = 5-[4-(N-Acetyl-4-chlorophenyl-sulfoximino)-butoxy]-3,3-dimethyl-indolin-2-one,
Q = 6-[4-(N-tert.benzoyl-3,4-dimethoxyphenyl-sulfoximino)-butoxy]-3,4-dihydrocarbostyril, and
R = 6-[4-(3,4-dimethoxyphenyl-sulfoximino)-butoxy]-3,4-dihydrocarbostyril:

1. PDE Inhibition

Principle cAMP is hydrolyzed to AMP by phosphodiesterase (PDE) from various sources, including blood platelets. PDE-inhibitors inhibit this hydrolysis, the PDE-inhibition being dependent on the concentration.

Method:

The phosphodiesterase used was prepared by centrifugal extraction at 10,000 G from human blood platelets which were frozen in water and then thawed.

0.3 ml of a mixture containing 0.1 mol/liter of trihydroxy-aminomethane (pH 7.4), 3 mmols/liter of magnesium chloride, 1 mmol/liter of AMP, 1 μmol/liter of $^3$H-cAMP (specific activity about 10 MBq/μmol), PDE and the inhibitor under investigation (water in the case of the control) was incubated for 15 minutes at 37° C. The incubation was stopped by the addition of 0.5 ml zinc sulfate (0.266 mol/liter) and 0.5 ml barium hydroxide (0.226 mol/liter), the precipitate was centrifuged, and the activity remaining in the unreacted $^3$H-cAMP in the supernatant was determined. From a comparison of the results for inhibitor and control cases, the concentration of the respective inhibitor necessary for a 50% inhibiting effect (IC$_{50}$) was calculated:

TABLE I

| Compound | IC$_{50}$ (μmol/liter) |
|---|---|
| A | 45 |
| B | 2.0 |
| C | 1.2 |
| D | 0.84 |
| E | 0.84 |
| F | 0.90 |
| G | 0.40 |
| H | 0.17 |
| I | 0.039 |
| K | 0.24 |
| L | 0.052 |
| M | 0.21 |
| N | 0.68 |
| O | 0.53 |
| P | 1.8 |
| Q | 3.1 |
| R | 1.6 |

The inhibiting effect on tumor metastasis can also be demonstrated, according to Gastpar et al. [see Thrombosis Research 5, 227–289 (1974)], as an effect which prevents tumor cell embolism. The test compound is administered before the transplanting of the tumor cells and the survival rate of the test animals, for example rats, is determined by comparison with controls.

2. Determination of the prolongation of bleeding time

Preliminary remarks:

Humans, as well as other warm-blooded animals have an ingenious mechanism, which protects them from blood loss through injury. This system consists of blood platelets (thrombocytes), which quickly seal up injured vessels due to their adhesive properties, thus bringing about primary hemastasis. Besides this purely cellular hemostatic mechanism, the body has a blood coagulation system. In this system plasma factors (proteins) are activated and finally convert liquid plasma fibrinogen to a fibrin coagulum. The system of primary hemostasis, which is regulated mainly by the thrombocytes but also by the prostacyclin activity of the blood vessel walls, and coagulation complement each other in their common aim of protecting the body effectively from blood loss.

With some diseases it is found that coagulation and thrombocyte aggregation also take place in intact blood vessels. The influence on the coagulation system of coumarin and heparin is known and can easily be measured using known coagulation tests wherein the coagulation time is prolonged under the influence of these substances. (Plasma recalcification time, Quick's test, thrombin time, etc.).

Since, in the event of injury, the first rapid cessation of bleeding is effected by the adhesion and aggregation of the thrombocytes at the vessel wall, the functioning of the thrombocytes or the prostacyclin activity of the vessel wall can easily be determined by measuring the bleeding time with a standardized injury. The normal bleeding time in humans is between 1 and 3 minutes, assuming that there are sufficient intact, effective thrombocytes. If the number of thrombocytes is normal and the bleeding time is prolonged, this signifies an abnormality in the thrombocytes and/or an increased prostacyclin activity in the vessel wall. This is found in some inborn errors of thrombocyte function. If, on the other hand it is desired to prevent spontaneous aggregation of the thrombocytes and occlusion in the arterial system by drugs, successful therapy affecting the thrombocytes or vessel wall should prolong the bleeding time. Therefore, using an antithrombotic substance, a prolongation of the bleeding time is expected, and a normal coagulation time, since the plasma coagulation system is not affected.

Literature: W. D. Keidel: *Kurzgefasstes Lehrbuch der Physiologie*, Georg Thieme Verlag, Stuttgart 1967, page 31: The process of hemostasis.

To measure the bleeding time, 2.5 mg/kg of the test compound were administered orally to conscious mice. After one hour, 0.5 mm of the tip of the tail of each mouse was cut off and the droplets of blood were gently removed with filter paper every 30 seconds. The number of drops of blood thus obtained give a bleeding time (5 animals per experiment).

The results of the following table represent the prolongation of the bleeding time in percent as compared to a control group:

TABLE II

| Compound | Prolongation of bleeding time in % after 1 hour |
|---|---|
| A | 73 |
| B | >161 |
| C | 125 |
| D | 53 |
| E | >194 |
| F | >212 |
| G | 85 |
| H | 78 |
| I | >275 |
| K | >180 |
| L | >191 |
| M | >191 |
| N | >184 |
| O | >233 |
| P | >169 |
| Q | >158 |
| R | >218 |

3. Acute toxicity

The acute toxicity of the compounds was determined in groups of 10 mice after oral administration of a single dose (observation period: 14 days):

| Compound | Approximate acute toxicity |
|---|---|
| A | 250 mg (0 out of 10 animals died) |
| B | 250 mg (0 out of 10 animals died) |
| C | 250 mg (0 out of 10 animals died) |
| D | 250 mg (0 out of 10 animals died) |
| E | 1000 mg (0 out of 10 animals died) |
| F | 250 mg (0 out of 10 animals died) |
| G | 250 mg (0 out of 10 animals died) |
| H | 250 mg (0 out of 10 animals died) |
| I | 250 mg (0 out of 10 animals died) |

In view of their pharmacological properties mentioned above, the novel compounds of the invention are useful for the prophylaxis of thromboembolic diseases as coronary infarct, cebebral, infarct, so-called transient ischaemic attacks and amaurosis fugax, for the prophylaxis of arteriosclerosis and for prophylaxis of metastasis.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.1 to 4 mgm/kg body weight, preferably 0.2 to 3 mgm/kg body weight, 2 to 4 times daily.

The following examples illustrate a few pharmaceutical compositions comprising a compound of the present invention as an active ingredient and represent the best modes contemplated of using the invention. The parts are parts by weight unless otherwise specified.

EXAMPLE 140

Coated tablets containing 4 mg of 6-[4-(N-acetyl-3,4-dichlorophenyl-sulfoximino)-butoxy]-3,4-dihydrocarbostyril The tablet cores are compounded from the following ingredients:

| Active ingredient | (1) | 4.0 parts |
|---|---|---|
| Lactose | (2) | 27.0 " |
| Corn starch | (3) | 14.5 " |
| Polyvinylpyrrolidone | (4) | 4.0 " |
| Magnesium stearate | (5) | 0.5 " |
| | | 50.0 parts |

Preparation:

Ingredients (1) to (3) are homogeneously moistened with an aqueous solution of (4), then screened through a 1 mm-mesh screen, dried and again screened through a 1 mm-mesh. After the addition of (5), the mixture is compressed to form tablet cores.

Tablet cores: 5 mm φ, biconvex, round.

Coating:

Usual sugar coating to give a finished weight of 70 mg.

EXAMPLE 141

Tablets containing 8 mg of 6-[4-(N-acetyl-3,4-dichlorophenyl-sulfoximino)butoxy]-3,4-dihydrocarbostyril The tablet composition is compounded from the following ingredients:

| Active ingredient | 8.0 parts |
|---|---|
| Lactose | 23.0 " |
| Corn starch | 14.5 " |
| Polyvinylpyrrolidone | 4.0 " |
| Magnesium stearate | 0.5 " |
| | 50.0 parts |

Preparation:
Analogous to the tablet cores in Example 140.
Description of tablets:
Weight: 50.0 mg
Diameter 5 mm, biplanar, faceted on both sides.

EXAMPLE 142

Suppositories containing 25 mg of 6-[4-(N-acetyl-3,4-dichlorophenyl-sulfoximino)butoxy]-3,4-dihydrocarbostyril The suppository composition is compounded from the following ingredients:

| | |
|---|---|
| Active ingredient | 0.025 parts |
| Hart fat (e.g. cocoa butter) | 1.695 parts |
| | 1.700 parts |

Preparation:
The hard fat is melted. At 38° C. the ground active ingredient is homogeneously dispersed in the melt. The mixture is cooled to 35° C. and poured into slightly precooled suppository molds.
Weight of suppository: 1.7 g.

EXAMPLE 143

Suspension containing 8 mg of 6-[4-(N-acetyl-3,4-dichlorophenyl-sulfoximino)-butoxy]-3,4-dihydrocarbostyril per 100 ml

| | |
|---|---|
| Active ingredient | 0.16 parts |
| Carboxymethylcellulose | 0.1 " |
| Methyl-p-hydroxybenzoate | 0.05 " |
| Propyl p-hydroxybenzoate | 0.01 " |
| Sucrose | 10.0 " |
| Glycerol | 5.0 " |
| 70% sorbitol solution | 20.0 " |
| Flavoring | 0.3 " |
| Distilled water q.s. ad | 100.0 parts by vol. |

Preparation:
The distilled water is heated to 70° C. The methyl and propyl p-hydroxybenzoates and the glycerol and carboxymethyl cellulose are dissolved therein by stirring. The mixture is cooled to room temperature and the active ingredient is added and homogeneously dispersed therein by stirring. After the sugar, sorbitol solution and flavoring have been added and dissolved therein, the suspension is evacuated, while stirring, to remove air.

EXAMPLE 144

Tablets containing 100 mg of 6-[4-(N-acetyl-3,4-dichlorophenyl-sulfoximino)-butoxy]-3,4-dihydrocarbostyril The tablet composition is compounded from the following ingredients:

| | |
|---|---|
| Active ingredient | 100.0 parts |
| Lactose | 80.0 " |
| Corn starch | 34.0 " |
| Polyvinylpyrrolidone | 4.0 " |
| Magnesium stearate | 2.0 " |
| | 220.0 parts |

Method of preparation:
The active ingredients, lactose and starch are mixed together and homogeneously moistened with an aqueous solution of the polyvinylpyrrolidone. After the moist mass has been screened (2.0 mm-mesh size) and dried in a rack drier at 50° C., it is screened again (1.5 mm-mesh size), and the lubricant is added. The finished mixture is compressed into tablets.
Weight of tablet: 220 mg
Diameter: 10 mm, biplanar, faceted on both sides and notched on one side.

EXAMPLE 145

Hard gelatin capsules containing 150 mg of 6-[4-(N-acetyl-3,4-dichlorophenyl-sulfoximino)-butoxy]-3,4-dihydrocarbostyril The capsule filler composition is compounded from the following ingredients:

| | |
|---|---|
| Active ingredient: | 150.0 parts |
| Dried corn starch | 180.0 " |
| Powdered lactose | 87.0 " |
| Magnesium stearate | 3.0 " |
| | 320.0 parts |

Preparation:
The active ingredient is mixed with the excipients, passed through a screen with a mesh size of 0.75 mm and homogeneously mixed in a suitable apparatus.
The final mixture is transferred into hard gelatin capsules.
Capsule contents: about 320 mg
Capsule shell: Hard gelatine capsule size 1.

EXAMPLE 146

Suppositories containing 150 mg of 6-[4-(N-acetyl-3,4-dichlorophenyl-sulfoximino)-butoxy]-3,4-dihydrocarbostyril The suppository composition is compounded from the following ingredients:

| | |
|---|---|
| Active ingredient | 150.0 parts |
| Polyethyleneglycol 1500 | 550.0 " |
| Polyethyleneglycol 6000 | 460.0 " |
| Polyoxyethylene sorbitan monostearate | 840.0 " |
| | 2000.0 parts |

Preparation:
After the suppository mass has been melted, the active ingredient is homogeneously distributed therein, and the melt is poured into pre-cooled molds.

EXAMPLE 147

Suspension containing 50 mg of 6-[4-(N-acetyl-3,4-dichlorophenyl-sulfoximino)-butoxy]-3,4-dihydrocarbostyril per 5 ml The suspension is compounded from the following ingredients:

| | |
|---|---|
| Active ingredient | 1.0 parts |
| Sodium salt of carboxymethylcellulose | 0.1 " |
| Methyl p-hydroxybenzoate | 0.05 " |
| Propyl p-hydroxybenzoate | 0.01 " |
| Sucrose | 10.0 " |
| Glycerol | 5.0 " |
| 70% sorbitol solution | 20.0 " |
| Flavoring | 0.3 " |
| Distilled water q.s. ad | 100 parts by vol. |

Preparation:

The distilled water is heated to 70° C. The methyl and propyl p-hydroxybenzoates are dissolved therein, while stirring, together with the glycerol and sodium salt of carboxymethylcelluose. The mixture is cooled to room temperature, and the active ingredient is added and homogeneously dispersed therein by stirring. After the sugar, sorbitol solution and flavoring having been added and dissolved, the suspension is evacuated, while stirring, to remove air.

EXAMPLE 148

Tablets containing 150 mg of 6-[4-(N-p-toluenesulfonyl-3,4-dichlorophenyl-sulfoximino)-butoxy]-3,4-dihydrocarbostyril The tablet composition is compounded from the following ingredients:

| Active ingredient | 150.0 parts |
|---|---|
| Powdered lactose | 89.0 " |
| Corn starch | 40.0 " |
| Colloidal silicic acid | 10.0 " |
| Polyvinylpyrrolidone | 10.0 " |
| Magnesium stearate | 1.0 " |
| | 300.0 parts |

Preparation:

The active ingredient is mixed with the lactose, corn starch and silicic acid, and the mixture is moistened with an aqueous 20% polyvinylpyrrolidone solution and passed through a screen with a mesh size of 1.5 mm.

The resulting granulate, dried at 45° C., is again passed through the screen and mixed with with the specified quantity of magnesium stearate. Tablets are compressed from the mixture.

Weight of tablets: 300 mg
Punch: 10 mm, flat.

EXAMPLE 149

Coated tablets containing 75 mg of 6-[4-(N-p-toluenesulfonyl-3,4-dichlorophenyl-sulfoximino)-butoxy]-3,4-dihydrocarbostyril The tablet core composition is compounded from the following ingredients:

| Active ingredient | 75.0 parts |
|---|---|
| Calcium phosphate | 93.0 " |
| Corn starch | 35.5 " |
| Polyvinylpyrrolidone | 10.0 " |
| Hydroxypropylmethylcellulose | 15.0 " |
| Magnesium stearate | 1.5 " |
| | 230.0 parts |

Preparation:

The active ingredient is mixed with calcium phosphate, corn starch, polyvinylpyrrolidone, hydroxypropylmethyl-cellulose and half the specified quantity of magnesium stearate. Using a tablet-making machine, compressed tablets with a diameter of about 13 mm are produced, which are then forced through a screen with a mesh size of 1.5 mm and mixed with the remaining quantity of magnesium stearate. The resulting granulte is compressed into tablets of the desired shape in a tablet-making machine.

Weight of core: 230 mg
Punch: 9 mm, convex.

The tablet cores thus produced are coated with a film consisting essentially of hydroxypropylmethylcellulose. The finished film-coated tablets are polished with beeswax.

Weight of coated tablet: 245 mg.

Any one of the other compounds embraced by formula I or a non-toxic, pharmacologically acceptable acid addition salt thereof may be substituted for the particular active ingredient in Examples 140 through 149. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

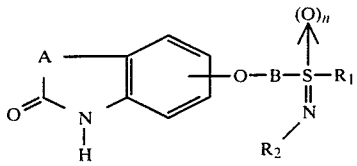

wherein n is 0 or 1;

A is vinylene or ethylene;

B is straight alkylene of 3 to 5 carbon atoms;

$R_1$ is alkyl of 1 to 6 carbon atoms; benzyl; phenylethyl; cyclohexyl; naphthyl; methoxy-naphthyl; α-, β- or γ-pyridyl; phenyl; 3- or 4-monosubstituted phenyl, where the substituent is alkyl of 3 or 4 carbon atoms, cyclohexyl, phenyl or fluorophenyl; monosubstituted phenyl, where the substituent is methyl, ethyl, methoxy, fluorine, chlorine or bromine; 3,4- or 3,5-disubstituted phenyl, where the substituents are each independently alkyl of 1 to 4 carbon atoms, methoxy, chlorine or bromine; 3,5-disubstituted 4-aminophenyl, 4-hydroxyphenyl or 4-methoxyphenyl, where the substituents are each independently chlorine, bromine, methoxy or alkyl of 1 to 4 carbon atoms; and $R_2$ is hydrogen alkanoyl of 1 to 8 carbon atoms; methoxy(alkanoyl of 1 to 8 carbon atoms); benzoyl; monosubstituted benzoyl, where the substituent is halogen, cyano or alkyl of 1 to 4 carbon atoms; phenylsulfonyl; (monosubstituted phenyl)sulfonyl, where the substituent is halogen, cyano or alkyl of 1 to 4 carbon atoms; (alkoxy of 1 to 3 carbon atoms)carbonyl; aminocarbonyl; (chlorophenylamino)carbonyl; methylamino-carbonyl; dimethylamino-carbonyl; naphthoyl; pinanoyl; camphorsulfonyl; (pentamethyl-phenyl)sulfonyl; 3-pyridinoyl; or 2-thenoyl;

or a non-toxic, pharmacologically acceptable addition salt thereof formed with a strong acid.

2. A compound of claim 1, where n is 1;

A is vinylene or ethylene;

B is butylene;

$R_1$ is methyl; methoxynaphthyl; phenyl; monosubstituted phenyl, where the substituent is methoxy, fluorine or chlorine; 3,4- or 3,5-disubstituted phenyl, where the substituents are each independently chlorine or bromine; (methyl)(bromo)phenyl; 4 amino-3,5-dibromophenyl; or 3,5-di-tert.butyl-4-hydroxyphenyl; and $R_2$ is hydrogen; alkanoyl of 1 to 3 carbon atoms; benzoyl; (alkyl of 1 to 4 carbon atoms)benzoyl; phenylsulfonyl; or (alkyl of 1 to 4 carbon atoms-phenyl)sulfonyl;

or a non-toxic pharmacologically acceptable addition salt thereof formed with a strong acid.

3. A compound of claim 2, where n is 1;

A is ethylene or vinylene;

B is n-butylene;

$R_1$ is methyl, phenyl, 4-fluorophenyl, 4-chlorophenyl, 3,4-dichlorophenyl or 3-methyl-4-bromophenyl; and $R_2$ is hydrogen, acetyl or p-toluenesulfonyl;

or a non-toxic pharmacologically acceptable addition salt thereof formed with a strong acid.

4. The compound of claim 2, which is 6-[4-(N-acetyl-3,4-dichloorophenyl-sulfoximino)butoxy]-3,4-dihydrocarbostyril.

5. The compound of claim 2, which is 6-[4-(3-methyl-4-bromophenyl-sulfoximino)-butoxyl]-carbostyril.

6. An antithrombotic pharmaceutical composition consisting essentially of an inert pharaceutical carrier and an effective antithrombotic amount of a compound of claim 2.

7. The method of preventing or relieving thrombosis in a warm-blooded animal in need thereof, which comprises perorally, parenterally or rectally administering to said animal an effective antithrombotic amount of a compound of claim 2.

* * * * *

UNITED STATES PATENT AND TRADEMARK OFFICE
CERTIFICATE OF CORRECTION

PATENT NO. : 4,551,464

DATED : Nov. 5, 1985

INVENTOR(S) : ERICH MÜLLER ET AL.

It is certified that error appears in the above-identified patent and that said Letters Patent is hereby corrected as shown below:

Column 2, line 56: "eh" should read -- ch --.

Column 3, line 20: "group substituted" should read -- group optionally substituted --.

Column 4, line 10: That portion of the formula which reads

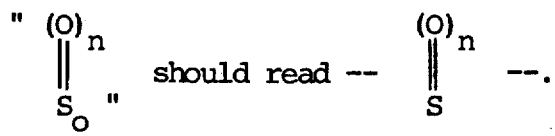

Column 7, line 35: "butoxy)-b" should read -- butoxy)- --.

Column 8, line 1: "-ulfox-" should read -- -sulfox- --.

Column 8, line 27: "utoxy]" should read -- butoxy] --.

Column 9, line 17: "6-]4" should read -- 6-[4 --.

Column 9, line 29: "b 3,4-" should read -- 3,4 --.

Column 13, line 8: "butoxy]-O-indolinone" should read -- -- butoxy]indolinone --.

UNITED STATES PATENT AND TRADEMARK OFFICE
CERTIFICATE OF CORRECTION

PATENT NO. : 4,551,464

DATED : Nov. 5, 1985

INVENTOR(S) : ERICH MÜLLER ET AL.

It is certified that error appears in the above-identified patent and that said Letters Patent is hereby corrected as shown below:

Column 31, line 28: " 3 4-" should read -- 3,4- --.

Column 38, line 38: "3 or 4" should read -- 3 to 4 --.

Column 38, line 49: "hydrogen alkanoyl" should read -- hydrogen; alkanoyl --.

Signed and Sealed this

Fifth Day of August 1986

[SEAL]

Attest:

DONALD J. QUIGG

Attesting Officer     Commissioner of Patents and Trademarks